(12) United States Patent
Zhao et al.

(10) Patent No.: US 8,891,079 B2
(45) Date of Patent: Nov. 18, 2014

(54) WAFER INSPECTION

(75) Inventors: Guoheng Zhao, Palo Alto, CA (US);
Jenn-Kuen Leong, San Jose, CA (US);
Mehdi Vaez-Iravani, Los Gatos, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 13/822,281

(22) PCT Filed: Dec. 7, 2011

(86) PCT No.: PCT/US2011/063849
§ 371 (c)(1),
(2), (4) Date: Sep. 19, 2013

(87) PCT Pub. No.: WO2012/082501
PCT Pub. Date: Jun. 21, 2012

(65) Prior Publication Data
US 2014/0009759 A1 Jan. 9, 2014

Related U.S. Application Data

(60) Provisional application No. 61/424,039, filed on Dec. 16, 2010.

(51) Int. Cl.
*G01N 21/00* (2006.01)
*G01J 4/00* (2006.01)
*G01N 21/88* (2006.01)
*G01N 21/95* (2006.01)
*H01L 21/66* (2006.01)

(52) U.S. Cl.
CPC ............ *G01N 21/8806* (2013.01); *H01L 22/12* (2013.01); *G01N 21/9501* (2013.01)
USPC ...................... 356/237.2; 356/237.5; 356/364; 356/369

(58) Field of Classification Search
CPC .................. G01N 21/9501; G01N 2021/8825; G01N 21/8806; G01N 21/95607; G01N 21/21; G01N 21/95623; G01N 2021/95676; G01N 21/47; G01N 21/956; G01N 2021/479; G01N 21/94; G01N 2201/06113; G01N 2021/4792
See application file for complete search history.

(56) References Cited

U.S. PATENT DOCUMENTS 4,854,705 A * 8/1989 Bachalo ......................... 356/336
5,717,485 A 2/1998 Ito et al.
(Continued)

FOREIGN PATENT DOCUMENTS

JP 2010-197352 9/2010

OTHER PUBLICATIONS

International Search Report and Written Opinion for PCT/US2011/063849 mailed Jun. 27, 2012.
(Continued)

*Primary Examiner* — Michael P Stafira
(74) *Attorney, Agent, or Firm* — Ann Marie Mewherter

(57) ABSTRACT

Systems and methods for inspecting a wafer are provided. One system includes an illumination subsystem configured to illuminate the wafer; a collection subsystem configured to collect light scattered from the wafer and to preserve the polarization of the scattered light; an optical element configured to separate the scattered light collected in different segments of the collection numerical aperture of the collection subsystem, where the optical element is positioned at a Fourier plane or a conjugate of the Fourier plane of the collection subsystem; a polarizing element configured to separate the scattered light in one of the different segments into different portions of the scattered light based on polarization; and a detector configured to detect one of the different portions of the scattered light and to generate output responsive to the detected light, which is used to detect defects on the wafer.

43 Claims, 13 Drawing Sheets

(56) References Cited

U.S. PATENT DOCUMENTS

| | | | |
|---|---|---|---|
| 6,034,776 | A | 3/2000 | Germer et al. |
| 6,201,601 | B1 | 3/2001 | Vaez-Iravani et al. |
| 6,366,690 | B1 * | 4/2002 | Smilansky et al. ........... 382/149 |
| 6,392,793 | B1 * | 5/2002 | Chuang et al. ................. 359/364 |
| 6,538,730 | B2 | 3/2003 | Vaez-Iravani et al. |
| 7,068,363 | B2 | 6/2006 | Bevis |
| 7,286,697 | B2 | 10/2007 | Guetta |
| 7,339,661 | B2 | 3/2008 | Korngut et al. |
| 7,385,688 | B1 | 6/2008 | Kadkly et al. |
| 7,436,505 | B2 | 10/2008 | Belyaev et al. |
| 7,489,393 | B2 | 2/2009 | Biellak et al. |
| 7,525,659 | B2 | 4/2009 | Furman et al. |
| 7,605,913 | B2 | 10/2009 | Bills et al. |
| 7,616,299 | B2 | 11/2009 | Okawa et al. |
| 7,728,965 | B2 | 6/2010 | Haller et al. |
| 7,746,459 | B2 | 6/2010 | Kadkly et al. |
| 7,826,049 | B2 | 11/2010 | Furman et al. |
| 7,843,558 | B2 | 11/2010 | Furman |
| 7,952,701 | B2 * | 5/2011 | Matsui ....................... 356/237.3 |
| 8,169,613 | B1 | 5/2012 | Biellak et al. |
| 2002/0145732 | A1 | 10/2002 | Vaez-Iravani et al. |
| 2008/0273193 | A1 | 11/2008 | Nishiyama et al. |
| 2009/0225399 | A1 | 9/2009 | Zhao et al. |
| 2009/0284737 | A9 | 11/2009 | Matsui |
| 2010/0182602 | A1 | 7/2010 | Urano et al. |
| 2010/0188657 | A1 | 7/2010 | Chen et al. |
| 2012/0044486 | A1 | 2/2012 | Chen et al. |
| 2013/0016346 | A1 | 1/2013 | Romanovsky et al. |

OTHER PUBLICATIONS

International Preliminary Report on Patentability for PCT/US2011/063849 mailed Jun. 27, 2013.

U.S. Appl. No. 61/569,611 to Chuang et al. filed Dec. 12, 2011.

* cited by examiner

WAFER INSPECTION

BACKGROUND OF THE INVENTION

1. Field of the Invention

This invention generally relates to systems and methods for inspecting a wafer. Certain embodiments relate to a wafer inspection system that can include various optical elements and polarizing elements, which in combination segment the collection numerical aperture of a collection subsystem thereby optimizing the system for detection of certain defects while also possibly suppressing detection of other defects.

2. Description of the Related Art

The following description and examples are not admitted to be prior art by virtue of their inclusion in this section.

Examples of commercially available wafer inspection systems include the Surfscan SP1, SP2, and SP3 systems, which are commercially available from KLA-Tencor, Milpitas, Calif., and which generally are single-spot, spiral-scanning systems using an ellipsoidal collector and a supplementary small lens collector that fills in the central numerical aperture (NA) portion missing from the ellipsoidal collector. Various examples of such systems are illustrated in commonly owned U.S. Pat. No. 6,201,601 to Vaez-Iravani et al., which is incorporated by reference as if fully set forth herein.

Some inspection systems are designed such that different detectors detect light scattered into separate, different parts of the collection NA of the system. For example, inspection systems that use acousto-optical device (AOD) spot scanning with multiple (e.g., 5) lens collectors dividing up the collection NA are described in commonly owned U.S. Pat. No. 7,605,913 to Bills et al., which is incorporated by reference as if fully set forth herein. Additional examples of inspection systems that use spiral spot scanning with multiple detectors (e.g., 8) dividing up the collection NA are shown and described in U.S. Pat. No. 7,616,299 to Okawa el al., which is incorporated by reference as if fully set forth herein. There are similar systems that use multiple lens collectors to divide up the full collection NA based on the same concept. U.S. Patent Application Publication No. 2009/0284737 to Matsui, which is incorporated by reference as if fully set forth herein, describes a concept of segmented collection NA by splitting a mirror collector. In addition, commonly owned U.S. Pat. No. 6,538,730 to Vaez-Iravani et al., which is incorporated by reference as if fully set forth herein, describes a way of achieving collection NA segmentation using fiber arrays.

Some inspection systems are designed to use one or more polarizers to suppress surface scattering from a wafer, possibly in combination with segmenting the collection NA of the system. For example, U.S. Pat. No. 6,034,776 to Germer et al., which is incorporated by reference as if fully set forth herein (hereinafter "Germer"), discloses the use of a polarizer to null the scattering from surface roughness. Three collection configurations are described, one embodiment that uses multiple collectors, another embodiment that uses fibers, and a third embodiment that uses a mirror collector. Commonly owned U.S. Pat. No. 7,436,505 to Belyaev et al., which is incorporated by reference as if fully set forth herein, discloses a computer-implemented method for maximizing signal-to-noise by configuring portions of the scattering hemisphere using an ellipsoidal mirror collector. Commonly owned U.S. patent application Ser. No. 12/618,620 by Biellak et al. filed Nov. 13, 2009, issued as U.S. Pat. No. 8,169,613 on May 1, 2012, which is incorporated by reference as if fully set forth herein, discloses a segmented polarizer mask with arbitrary polarization.

Additional inspection systems are designed to reduce surface scattering by reducing the size of the illumination spot on the wafer and compensating for the reduced size of the spot by illuminating multiple spots on the wafer simultaneously. For example, commonly owned U.S. Pat. No. 7,358,688 to Kadkly et al., which is incorporated by reference as if fully set forth herein, discloses oblique one-dimensional multiple spot arrays with a lens collector. The systems include a unique illumination lens design that generates the one-dimensional spot array for oblique illumination. The illumination optics include tilted/decentered aspheric elements to generate the one-dimensional spot array that is tilted with respect to the tangential direction so that each spot scans adjacent tracks, while the incident plane is parallel to the radial direction of the wafer. Also shown in the patent is a high NA lens collector concept. Commonly owned U.S. Pat. No. 7,489,393 to Biellak et al., which is incorporated by reference as if fully set forth herein, discloses another way to generate a one-dimensional spot array at an oblique illumination angle. The proper tilt angle of the spot array with respect to the tangential direction is achieved by tilting the incident plane with respect to the radial direction.

Some of the systems described above have a number of disadvantages. For example, some of the systems described above are optimized (e.g., for maximum signal-to-noise ratio (SN), minimum haze, or maximum capture rate) based on mapping of surface scattering on the scattering hemisphere in spherical coordinates. For example, Germer discovered that the polarization of surface scattering changes with scattering angle and therefore proposed using multiple collectors distributed over the scattering hemisphere so that each one can be optimized independently to accommodate the change of polarization from surface scattering. In particular, Germer states:

It is beneficial to employ as many individual collection systems as possible, thus reducing the solid angle 'seen' by each; by doing so, the total system will better discriminate against surface microroughness, since the polarization due to microroughness will vary over any finite solid angle. For a finite solid angle, the discrimination is limited by the changing polarization state over that solid angle. (Germer—col. 7, lines 17-23).

Some inspection system architectures described in the above-referenced patents using multiple collectors to divide up the scattering hemisphere seem to be heavily influenced by Germer's arguments.

The disadvantages of the above-referenced systems can be described based on the similarities among the various inspection systems. For example, for "hard-wired" segmentation of the collection NA (e.g., collection that uses multiple lens collectors to divide the hemisphere of scattering into multiple segments), one disadvantage that such systems have in common is that the segmentation of the NA is fixed and is therefore difficult to reconfigure to optimize the systems for different samples and defects. In this manner, such configurations may have less than optimum performance for various defect types. Another disadvantage of such systems is that the majority of the collector optics is at a tilted angle with respect to the wafer surface normal. Therefore, it is difficult, if not impossible, to image multiple spots onto a detector array. As such, these configurations are not compatible with multi-spot illumination. In addition, the collection is also less efficient due to gaps between collectors.

For mirror-based, large NA collection (e.g., collection that uses a single large NA collector that is based on a mirror, e.g., ellipsoidal or parabolic), the disadvantage of using a mirror collector is that the polarization changes upon reflection due to the substantially large phase shift between p and s polarization. This effect scrambles the well-aligned nearly linear polarization of surface scattering from smooth silicon wafer surfaces, making it substantially difficult to use a polarizer to suppress the surface scattering and therefore undermines a capability to improve defect sensitivity.

With regard to using polarized collection to null surface scattering, Germer first disclosed the method of using polarization of collection to suppress the surface scattering. Some of the other patents referenced above also disclose the use of orthogonal polarization of detection to improve signal-to-noise for specific defects. There are two disadvantages to this approach: 1) the collection hemisphere is divided into multiple separate collection solid angles rendering the system complex and the collection efficiency low; and 2) the polarization of scattered light is mapped onto the surface of a hemisphere, across which the polarization of scattered light changes with scattering angle. This second disadvantage is the main reason that in previously used systems the hemisphere has to be divided up (so that over each relatively small aperture, the polarization of surface scattering is approximately aligned).

With regard to the previously used multi-spot illumination systems, in the existing one-dimensional multi-spot illumination concepts, each spot scans adjacent tracks on the wafer, which requires magnification (in addition to beam size expansion) changes for both illumination and collection when the spot size changes. For example, the spacing in the radial direction between spots needs to change when the spot size changes, which can result in pitch changes between tracks. These and other disadvantages of currently used multi-spot inspection systems are described in commonly owned U.S. Patent Application Publication No. 2009/0225399 to Zhao et al., which is incorporated by reference as if fully set forth herein.

Accordingly, it would be advantageous to develop an architectural approach for future generations of bare wafer inspection systems that enables significant improvements in the achievable signal-to-noise ratio for substantially small particles on bare wafers without one or more of the disadvantages of the currently used inspection systems.

SUMMARY OF THE INVENTION

The following description of various embodiments is not to be construed in any way as limiting the subject matter of the appended claims.

One embodiment relates to a system configured to inspect a wafer. The system includes an illumination subsystem configured to illuminate the wafer. The system also includes a collection subsystem configured to collect light scattered from the wafer and to preserve the polarization of the scattered light. In addition, the system includes an optical element configured to separate the scattered light collected in different segments of the collection numerical aperture (NA) of the collection subsystem. The optical element is positioned at Fourier plane or a conjugate of the Fourier plane of the collection subsystem. The system further includes a polarizing element configured to separate the scattered light in one of the different segments into different portions of the scattered light based on polarization. The system also includes a detector configured to detect one of the different portions of the scattered light and to generate output responsive to the detected light. The output is used to detect defects on the wafer.

The system described above may be further configured as described herein. For example, the collection subsystem may be configured to collect the light scattered from the wafer over a relatively large NA. The collection subsystem may include a lens collector that does not alter the polarization of the scattered light.

The optical element (and possibly other optical elements described herein) may function as an NA segmentation subsystem configured to divide the full collection NA of the collection subsystem into different segments and to direct the scattered light collected in the different segments to separate detectors. In one example, the optical element may include an apertured mirror that reflects scattered light collected in one segment of the collection NA while transmitting scattered light collected in another segment of the collection NA. The optical element may be configured to optimize each segment of the collection NA for maximum signal-to-noise ratio for various defect types. One or more reflective portions of the optical element may have a thin film coating formed thereon such that phase retardation is cancelled (or substantially canceled) upon an even number of reflections.

In addition, the polarizing element may be configured to separate two independent polarization components of the scattered light in a segment of the collection NA. The orientation of the polarization of the polarizing component may be mirror symmetric with respect to the incident plane. The polarization(s) of the light detected by the detector and any other detectors included in the system (each detection channel) may be determined by optimization of (maximizing) the signal-to-noise ratio of the output generated by each detector.

As described further herein, one detector included in the system may be optimized for substantially high sensitivity to particles by optimizing the polarization and one or more characteristics (e.g., shape) of the segment of the collection NA detected by the detector such that the scattering from the wafer surface and, at the same time, the loss of scattering from particles are minimized thereby maximizing the signal-to-noise ratio of the particles. Other detectors may be optimized for substantially high sensitivity to other defect types such as scratches, pits, and stains in a similar manner (e.g., by configuring the polarization of the scattered light and the characteristic(s) of the segments of the collection NA directed onto the corresponding detectors). Each of these embodiments of the system may be further configured as described herein.

Another embodiment relates to a method for inspecting a wafer. The method includes illuminating the wafer. The method also includes collecting light scattered from the wafer using a collection subsystem. The collection subsystem is configured to preserve the polarization of the scattered light. In addition, the method includes separating the scattered light collected in different segments of the collection NA of the collection subsystem using an optical element. The optical element is positioned at a Fourier plane or a conjugate of the Fourier plane of the collection subsystem. The method also includes separating the scattered light in one of the different segments into different portions of the scattered light based on polarization using a polarizing element. In addition, the method includes detecting one of the different portions of the scattered light to generate output responsive to the detected light. The method further includes detecting defects on the wafer using the output.

Each of the steps of the method described above may be further performed as described herein. In addition, each of the steps of the method may be performed using any of the system(s) described herein. Furthermore, the method may include any other step(s) that can be performed by any of the system(s) described herein. For example, the collection subsystem used in the method may include polarization preserving collection optics that may be configured as described herein. In addition, separating the scattered light collected in different segments of the collection NA may include dividing the full collection NA into multiple detection channels. The optical element and the polarizing element used in the method may be configured to optimize detection of one of the different portions of the scattered light for high sensitivity to particles. Therefore, a system used to perform the method may include a detection channel that is optimized for high sensitivity to particles. For example, a shape of a segment of the collection NA for a particle sensitive detection channel and the polarization of the light detected by the particle sensitive detection channel may be configured to minimize detection of scattering from the wafer surface (noise) and maximize collection and detection of scattering from the particles (signal). Other channels included in a system configured to perform the method may be optimized for best sensitivity to other defect types in a similar manner.

BRIEF DESCRIPTION OF THE DRAWINGS

Other objects and advantages of the invention will become apparent upon reading the following detailed description and upon reference to the accompanying drawings in which.

Figure 1A:
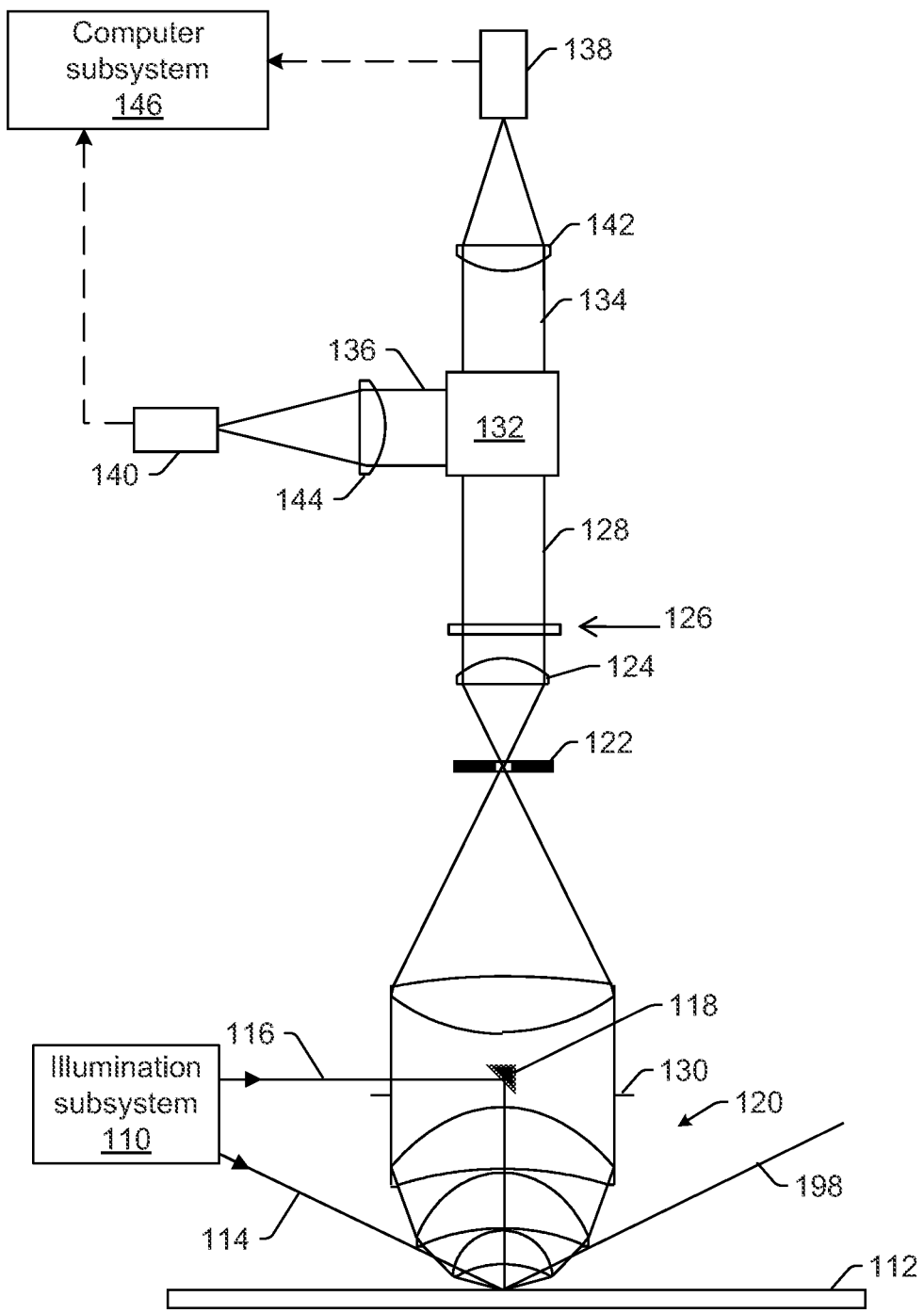
FIGS. 1a-1d are schematic diagrams illustrating side views of various embodiments of a system configured to inspect a wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

FIG. 1a illustrates one embodiment of a system configured to inspect a wafer. The system includes an illumination subsystem configured to illuminate the wafer. For example, illumination subsystem 110 may be configured to illuminate wafer 112 by directing oblique illumination 114 to the wafer and/or normal illumination 116 to the wafer. For example, the illumination subsystem may include a number of optical elements such as reflective optical element 118 configured to direct light from one or more light sources (not shown) to the wafer at one or more desired angles of incidence.

The illumination subsystem may also be configured such that light is directed to the wafer at an oblique angle of incidence and/or a normal or substantially normal angle of incidence, but not both at the same time. For example, the system may be configured to move one or more optical elements (not shown) of the illumination subsystem depending on which type of illumination is to be used for inspection (e.g., based on a type of wafer to be inspected). In one such example, the system may be configured to move a shutter (not shown) into the path of the oblique angle of incidence illumination if only normal or substantially normal angle of incidence illumination is to be used for inspection or vice versa. The system may be configured to move one or more optical elements of the illumination subsystem in any suitable manner known in the art.

The illumination subsystem may include one or more light sources (not shown). The light source(s) may include any suitable light source such as a laser, a cw laser, or a pulsed laser. In addition, the light source(s) may be configured to generate light at any suitable wavelength(s) (e.g., about 355 nm, about 266 nm, or about 193 nm). The polarization of illumination can be p-polarized, s-polarized, or circularly polarized. In one embodiment, the illumination subsystem is configured to illuminate the wafer by directing only p-polarized light to the wafer. For example, the illumination subsystem may include a light source (not shown) that is configured to generate only p-polarized light. In addition, the illumination subsystem may include a light source (not shown) that is configured to generate light and a polarizing element (not shown) positioned in the path of the light and that is configured to transmit only p-polarized light such that only p-polarized light is directed to the wafer.

In another embodiment, the illumination subsystem is configured to illuminate the wafer by directing only s-polarized light to the wafer. Such an illumination subsystem may be configured as described above. In addition, the illumination subsystem may be configured to illuminate the wafer by directing light to the wafer, and the light has a polarization that is selected based on one or more characteristics of the wafer. For example, p-polarized illumination may be used for best particle sensitivity. However, other polarizations such as s-polarized light may have better performance for other types of wafers such as those having a rough film formed thereon. A computer subsystem such as that described further herein may be configured to determine one or more characteristics of the wafer in any suitable manner and to select the polarization of the illumination based on the characteristic(s) in any suitable manner.

In one embodiment, the illumination subsystem is configured to simultaneously illuminate an array (not shown in FIG. 1a) of spaced apart spots on the wafer. For example, light from a light source may be directed to a diffractive optical element (DOE) (not shown) of the illumination subsystem. The DOE may include any suitable DOE. The DOE may be configured to separate the light from the light source into two or more individual beams. The DOE may be configured to separate the light into any suitable number of individual beams. The array of spots on the wafer may be a one-dimensional array of spots. The spots do not overlap with each other on the wafer. In addition, a size of each of the spots on the wafer may be approximately equal.

Figure 2:
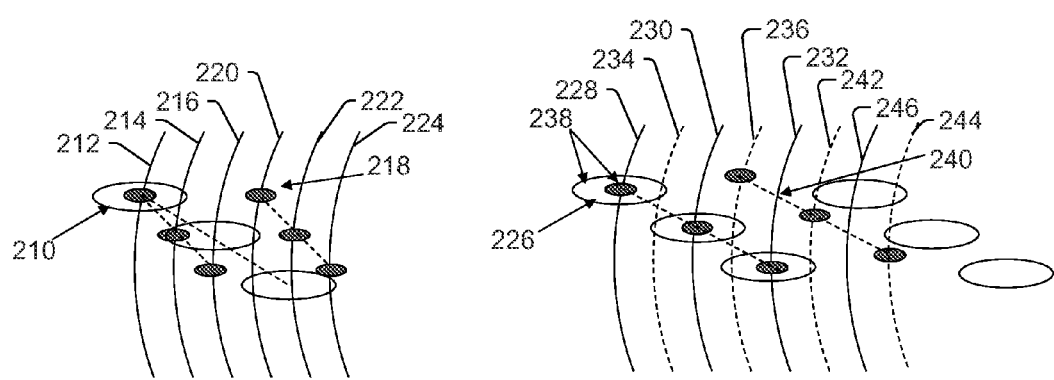
FIG. 2 is a schematic diagram illustrating a plan view of one example of a previously used array of simultaneously illuminated spots on a wafer and one embodiment of an array of simultaneously illuminated spots on a wafer.

In one embodiment, the spots are spaced apart on the wafer such that adjacent spots in the array scan tracks on the wafer that are spaced apart by more than a width of the tracks. In this manner, there will be a skipped track between the tracks that are scanned by two adjacent spots in the array. For example, as shown in FIG. 2, the solid and open ellipses represent different sizes of spots, and the curved lines represent the center of the tracks that are scanned on the wafer. In previously used multi-spot illumination in which the spots in an array are spaced from each other such that adjacent spots scan adjacent tracks on the wafer, when the spots have a smaller size corresponding to a size approximately 2× a width of the tracks, in swath 210 (e.g., swath n), the three adjacent spots will scan three adjacent tracks 212, 214, and 216 on the wafer. In the next swath 218 (e.g., swath n+1), the three adjacent spots will scan the next three adjacent tracks 220, 222, and 224 on the wafer. As shown in FIG. 2, swaths 210 and 218 are adjacent to one another on the wafer (i.e., the swaths do not overlap on the wafer except perhaps in regions near the edges of the swaths such that the whole wafer can be scanned). In this manner, the entire surface area of the wafer can be scanned by the spots.

However, if the sizes of the spots should increase (from the sizes represented by the solid ellipses to the sizes represented by the open ellipses) so that higher throughput can be achieved, then the width of tracks that are scanned by the spots also increases accordingly, which results in the increase of spacing between spots. Additional optics and automated mechanics are needed to change the optics magnification of both illumination and collection to accommodate the change of spot spacing, therefore increasing the complexity and cost.

In contrast, in embodiments described herein, in swath 226 (e.g., swath n), adjacent spots in an array may scan tracks 228, 230, and 232, each of which is spaced apart on the wafer from the other tracks in the swath by more than a width of a track (e.g., track 234 or 236 interposed between the tracks scanned in swath 226). In other words, adjacent spots in an array scan every other track on the wafer (or at least not tracks that are adjacent to one another (e.g., every third or every fourth track on the wafer)). In this manner, should the size of the spots increase (e.g., by double or 2×), the width of track also increases by the same factor (e.g., by 2×), then the spot spacing can be maintained the same while only the swath width changes by the same factor. For example, if spot 238 increases in size (e.g., by 2×) from the size shown by the solid ellipse to the size shown by the open ellipse, spot 238 would still scan track 228 for swath n, and then scan the track 246 for swath n+1. In other words, the spot spacing would remain the same regardless of the sizes of the spot so that there would be no need for additional optics in either illumination or collector for changing optics magnification.

In addition, in previously used multi-spot scanning schemes, the inspection systems are generally designed such that swaths (e.g., swaths 210 and 218) do not overlap on the wafer except near the edges of the swaths. In this manner, the swaths are arranged side by side on the wafer such that the swaths cover the whole wafer. In contrast, in the embodiments described herein, the swaths may overlap one another such that unscanned tracks in a swath, which are between tracks that are scanned in the swath, may be scanned in the next or another swath. For example, as shown in FIG. 2, in swath 240 (e.g., swath n+1), adjacent spots in the array may scan track 236 that is located between tracks 230 and 232 that were scanned in swath 226 (e.g., swath n), track 242, and track 244. In addition, as shown in FIG. 2, track 246 that is located between tracks 242 and 244 may not be scanned in swath 240.

In this manner, the illumination subsystem may be configured for one-dimensional relatively sparse multi-spot illumination, which advantageously simplifies the optics in the system for variable spot size. For example, the relatively sparse multi-spot concept is advantageous in that no magnification changers are required to account for variable spot size thereby resulting in a much simpler system. In addition, the relatively sparse multi-spot concept relaxes the requirements for the collection subsystem described further herein thereby lowering the cost of the optics. Furthermore, the inspection system may also be extendable to multiple generations. The illumination subsystem may be further configured for sparse multi-spot illumination as described in commonly owned U.S. patent application Ser. No. 12/042,252 by Zhao et al. filed Mar. 4, 2008, published as U.S. Patent Application Publication No. 2009/0225399 on Sep. 10, 2009, which is incorporated by reference as if fully set forth herein.

The illumination subsystem may alternatively be configured to illuminate the wafer by directing light to only a single spot on the wafer. As such, the system may be configured for single or multiple spot illumination.

Referring back to FIG. 1a, the system also includes collection subsystem 120 configured to collect light scattered from the wafer and to preserve the polarization of the scattered light. For example, in one embodiment as shown in FIG. 1a, collection subsystem 120 includes a lens collector configured to collect the light scattered from the wafer. In this embodiment, the collection subsystem does not include any reflective optical elements, and the collection subsystem does not alter the polarization of the scattered light. In this manner, the collection subsystem may be optimized for preserving polarization transmission without phase retardation. For example, the collection subsystem may be optimized for preserving polarization because the collection subsystem does not have any reflective surfaces. Therefore, the polarization of light will not change when the light is transmitted through the collection subsystem (compared to reflection). In other words, the collection subsystem is polarization preserving versus the relatively large phase retardation generated by previously used mirror collectors (resulting in a polarization change), which is described further herein. However, the collection subsystem may be optimized for preserving polarization in other manners described further herein.

The lens collector may also have a relatively simple design and a minimum number of elements. For example, as shown in FIG. 1a, the tens collector may include only four refractive optical elements, which may include any suitable refractive optical elements known in the art. In addition, the lens collector may include any suitable number of refractive optical elements. In one embodiment, the collection subsystem comprises a scattered light collector (e.g., the lens collector shown in FIG. 1a) having a numerical aperture (NA) greater than 0.9. For example, the scattered light collector may have an NA of about 0.90 to 0.97. In this manner, the scattered light collector may be an ultra-high NA collector. Therefore, the system may include a relatively simple and low cost high NA collector. In addition, if the illumination subsystem is configured to illuminate multiple spots on the wafer simultaneously, the lens collector may be configured to have good imaging performance so that the multiple spots of illumination are clearly separated when imaged onto a detector or detector array.

In another embodiment, the collection subsystem includes only one scattered light collector (e.g., only the lens collector shown in FIG. 1a). In this manner, the collection subsystem may include a single scattered light collector that is configured to collect the light scattered from the wafer. For example, as described further herein, some inspection systems are designed to segment the light scattered from a wafer in collection space of an inspection system by using multiple, separate lens collectors, which are positioned such that each of the lens collectors collects light in a different portion of the collection space. Unlike those systems, as described further herein, the light may be collected by a single scattered light lens collector, and then the collected light may be segmented, which is advantageous as described herein.

In another embodiment, the collection subsystem includes only one scattered light collector configured to collect light scattered across substantially the entire scattering hemisphere of the collection subsystem. In this manner, the collection subsystem may include a single scattered light collector that is configured to collect light scattered from the wafer over a substantially large NA. As such, unlike previously used systems that include multiple collectors, each of which collects light scattered into only a relatively small portion of the entire collection space of a collection subsystem, the embodiments described herein may include a single scattered light collector that collects light across a substantially large portion (e.g., the entirety) of the collection NA and then the scattered light that has been collected by the single scattered light collector can be divided as described further herein.

In an additional embodiment, the system includes only one collection subsystem configured to collect light scattered from the wafer. For example, although the system may include another collection subsystem configured to collect light reflected from the wafer, which may be configured as described herein, the system preferably includes only one scattered light collection subsystem. In this manner, the system is also different from previously used systems, which can be considered to include multiple scattered light collection subsystems, each of which collects light scattered into only a portion of the entire collection space of the system. In other words, as described further herein, the system includes a single scattered light collection subsystem, which in of itself includes only a single scattered light collector. However, the single scattered light collector itself may include more than one optical element (as shown in FIG. 1a) that in combination (in series) make up the single collector.

The system also includes an optical element that is configured to separate the scattered light collected in different segments of the collection NA of the collection subsystem. In this manner, the optical element may function as an NA segmentation subsystem configured to divide the collection NA into multiple segments. In one embodiment, the system includes a field stop positioned in the path of the collected light. For example, as shown in FIG. 1a, the system may include field stop 122. The field stop is configured to reject light scattered from air molecules near a surface of the wafer in one or more paths of one or more light beams used by the illumination subsystem to illuminate the wafer. For example, the field stop may have opening(s) that are slightly larger than the spot size(s) projected by the collector lens. Therefore, the field stop may effectively block the unwanted stray light and scattered light from ambient air molecules in the path of light beam(s) (e.g., laser beam(s)) near the illumination spot(s) on the wafer. In the case of multi-spot illumination, the field stop may include multiple openings to match the multiple spot illumination or a slit that is parallel to the line of spots in an array.

The collection subsystem is configured to focus the collected scattered light through field stop 122 to relay optics 124, which may be configured as described further herein. The collected scattered light may be transmitted by relay optics 124 to optical element 126. The optical element is configured to separate the scattered light collected in different segments of the collection NA of the collection subsystem. For example, as shown in cross-sectional views described further herein, the optical element may include portion(s) that reflect the collected scattered light and other portion(s) that transmit the collected scattered light. In the case of FIG. 1a, for example, optical element 126 is configured to separate scattered light 128 that is collected in one segment of the collection NA of the collection subsystem from other scattered light (not shown) that is collected in another segment of the collection NA by transmitting scattered light 128 in one segment while reflecting the other scattered light in another segment. However, the optical element may separate the scattered light in the different segments using reflection, blocking, refraction, diffraction, absorption, or any other suitable optical technique.

The optical element may include various optical elements such as an aperture, a mask, an apertured mirror, a liquid crystal display (LCD) element, or a micro-minor array. In one such example, a suitable aperture may be formed by cutting out a portion of a folding mirror such that one portion of the mirror transmits light while another portion of the folding mirror reflects light. In another such example, an apertured mirror can be manufactured by forming a masking coating of metal film(s) and/or dielectric film(s) on a transparent substrate. The segmentation of the collection NA can also be realized by using other beam splitting optical elements such as prisms with various facet orientations to refract the light in different directions. Other means of segmenting the collection NA are also possible, including micromirror devices such as those commonly used in digital light projectors.

The optical element is preferably positioned at a Fourier plane or a conjugate of the Fourier plane of the collection subsystem. For example, the collection subsystem may have accessible Fourier plane 130. In this manner, unlike most traditional objective lens designs that have the Fourier plane located inside the objective lens assembly and thus not physically accessible, the collection subsystem described herein is designed to have the Fourier plane located in a position where one can physically put an optical element such as an aperture or mask. The position of optical element 126 shown in FIG. 1*a* is the position of the conjugate of the Fourier plane of the collection subsystem. However, the optical element may also be positioned at Fourier plane 130 shown in FIG. 1*a*. In addition, "at a Fourier plane" or "at a conjugate of the Fourier plane" is defined herein to mean not only just at exactly the Fourier plane or at exactly the conjugate of the Fourier plane. Instead, those terms are intended to mean "at or near a Fourier plane" and "at or near a conjugate of the Fourier plane," respectively. An optical element as described herein can be considered to be "at or near a Fourier plane" if it is positioned at the exact location of the Fourier plane or at a position that is within about 5% error of the exact location of the Fourier plane (due to whatever error sources are in the system and/or physical constraints in the system). "At or near a conjugate of the Fourier plane" can be described in a similar manner. The optical element 126 can also be placed away from the Fourier plane but at a substantial distance from field stop 122 if somewhat degraded performance is acceptable. The performance degradation is dependent on the field of view of the lens collector 120, which can be minimal for single spot illumination.

The optical element (and other optical elements described herein) is used to separate the collection NA into different segments such that the scattered light in the different segments can be directed to different channels of the system. For example, as described above, the optical element may have one portion that reflects light and another portion that transmits light. Therefore, the optical element may separate the collection NA into two segments, one segment of which is directed into one channel by reflection and another segment of which is directed into another channel by transmission. In this manner, the optimization is performed at a Fourier plane (or a conjugate of a Fourier plane) versus on the surface of a hemisphere as is currently performed.

In one embodiment, the scattered light is mapped onto the Fourier plane using vector Fourier transformation. Vector Fourier transformation involves calculating the Fourier transform of the x, y, and z components of the vector electric field separately, recombining them at the image plane, and then taking the sum of the intensity. In this manner, surface scattering may be mapped onto the Fourier plane by vector Fourier transformation. As such, the polarization of surface scattering may be aligned substantially parallel across the Fourier plane by using vector Fourier transform. Therefore, in some embodiments, the polarization of the collected light due to surface scattering from the wafer is substantially parallel across a substantial portion of the Fourier plane and/or the conjugate of the Fourier plane. In other words, as a result of the Fourier transform described above, the polarization of surface scattering is aligned nearly parallel. As such, the polarization of surface scattering may be aligned substantially parallel across a substantial portion of the Fourier plane in contrast to the varying polarization on a hemisphere of previously used systems.

Figure 3:
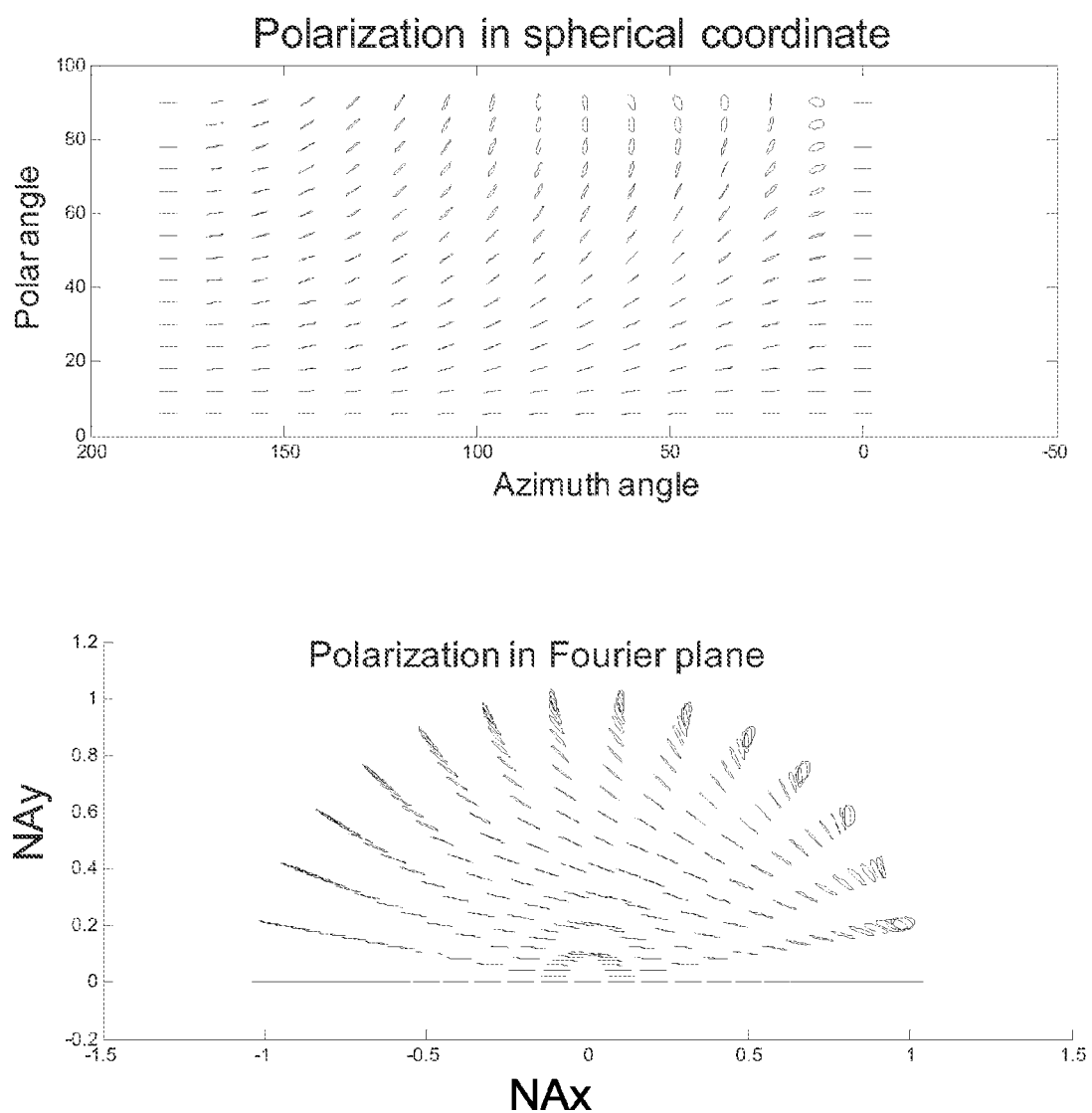
FIG. 3 includes plots showing the polarization of scattered light across a hemisphere of a lens collector and in the Fourier plane of the lens collector.

In this manner, the polarization of the scattered light from the wafer surface may be aligned substantially parallel in the plane in which segmentation is performed in the systems described herein in contrast to the varying polarization in the hemisphere in which segmentation has been performed in previously used systems. For example, FIG. 3 shows the difference between the polarization of surface scattering when projected onto a Fourier plane and when projected onto the surface of a hemisphere. In particular, the small tines in both plots in FIG. 3 are the polarization of the surface scattering at different positions across a scattering hemisphere and across a Fourier plane. The plot shown in the top portion of FIG. 3 is the polarization in a hemisphere as a function of the spherical coordinates, polar angle and azimuth angle. Therefore, the plot at the top of FIG. 3 shows the polarization across the hemisphere as though the hemisphere was unfolded into the plane of the paper. The plot shown in the bottom portion of FIG. 3 is the polarization of the surface scattering in the Fourier plane as a function of NA in the x direction (i.e., NAx) and NA in the y direction (i.e., NAy). As shown in FIG. 3, at the Fourier plane, the polarization is better aligned in a similar direction over a fairly large area, thereby allowing more efficient suppression of surface scattering.

At the same time, because the surface scattering can be efficiently suppressed over a substantially large area of the collection NA, the scattered light from defects (e.g., particles) on the wafer can be collected and detected over a substantially large area, particularly compared to the relatively small segments of collection NA that have been used previously to optimize detection of particles or other defects. More specifically, since, in previously used systems, the surface scattering could be suppressed over only a relatively small segment of the collection NA, the scattered light from defects that was available for detection was limited by that relatively small area across which surface scattering could be suppressed. In contrast, in the embodiments described herein, surface scattering can be suppressed across a substantially large area within the collection NA, which allows more efficient collection of the scattering from defects (e.g., particles the wafer. As such, defect scattering within the substantially large area can be detected thereby increasing (e.g., maximizing) the signal-to-noise ratio.

The system also includes a polarizing element configured to separate the scattered light in one of the different segments into different portions of the scattered light based on polarization. For example, as shown in FIG. 1*a*, the system may include polarizing element 132 configured to separate the scattered light in the one segment transmitted by optical element 126 into portions 134 and 136. In particular, the polarizing element is configured to separate the two independent polarizations of the portion of the scattered light collected in the segment of the collection NA transmitted by optical element 126.

In one embodiment, the polarizing element has mirror symmetry with respect to an incident plane of the illumination subsystem. For example, when the illumination polarization is either parallel to the incident plane (e.g., p polarization) or perpendicular to the incident plane (e.g., s polarization), the polarization of the scattered light will have symmetry to the incident plane. Therefore, linear polarizers used in the collection paths for optimizing sensitivity for any type(s) of defects preferably have mirror symmetry to the incident plane.

In another embodiment, the polarizing element is a linear polarizer. For example, a commercially available linear polarizer can be used as well. In particular, when such a polarizing element is orientated either parallel or perpendicular to the incident plane, the polarization is naturally symmetric with respect to the incident plane and therefore may be considered a special case of a mirror symmetric polarizing element. In a similar manner, in one embodiment, the polarizing element is a polarizing beam splitter. The polarizing beam splitter may include any suitable polarizing beam splitter known in the art. In addition, the polarizing element may be a polarizing beam splitter with mirror symmetric polarization orientation. A linear polarizer or a polarizing beam splitter used as the polarizing element may therefore be configured to separate the light in one segment based on polarization into two different portions of the scattered light, which have different, orthogonal, and mutually exclusive polarizations.

Figure 4:
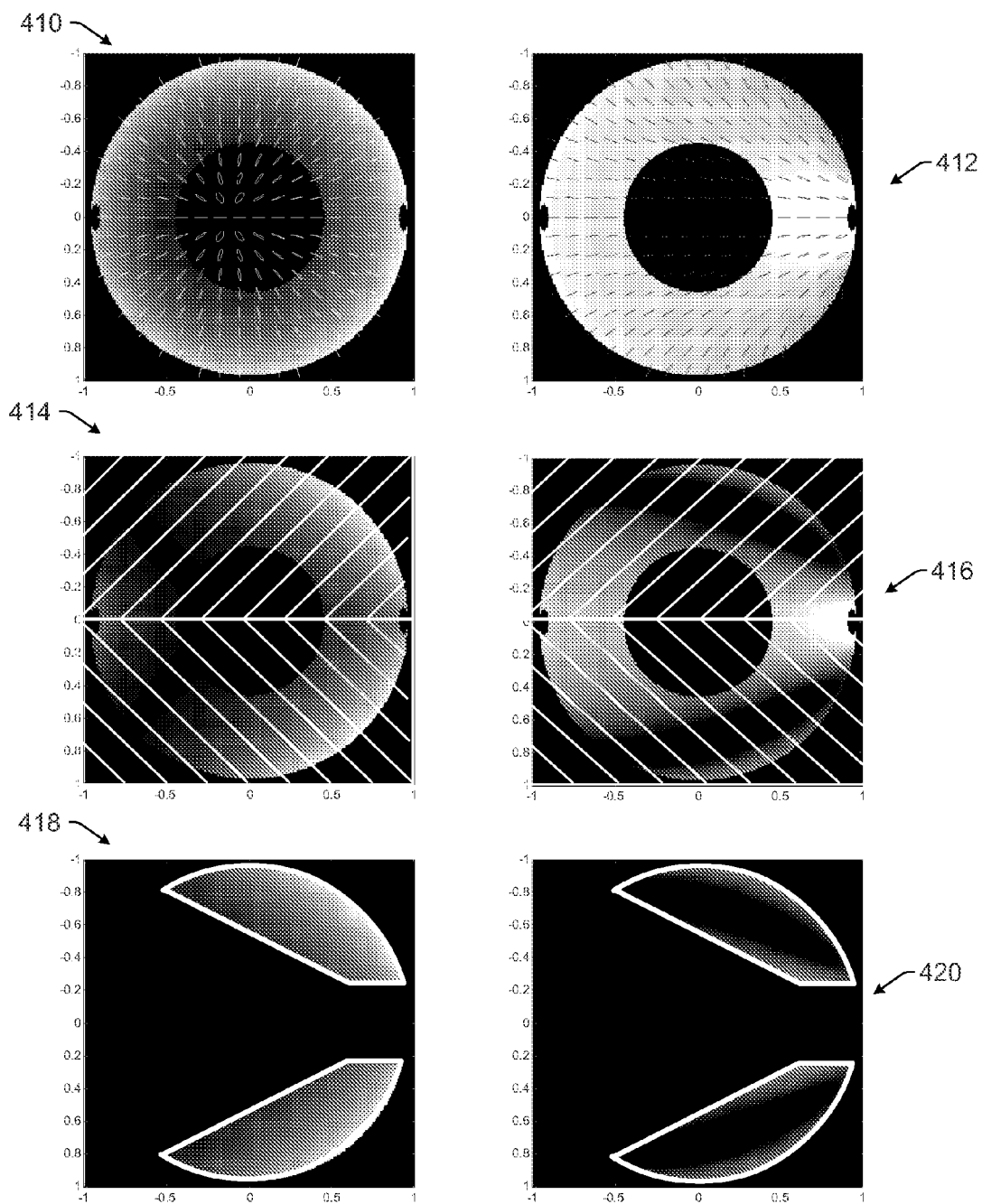
FIG. 4 is a schematic diagram illustrating one example of the intensity and polarization of particle and surface scattering and one embodiment of the shape of two individual segments of a collection numerical aperture (NA) and optimum polarization orientation that can be used in system embodiments described herein for high sensitivity for detecting substantially small particles.

The performance improvement in the inspection system due to the combination of separating the collected scattered light into different segments of the collection NA and a mirror symmetric polarizing element was determined by theoretical simulation and is shown in FIG. 4. The grayscale shown in the plots of FIG. 4 represents the intensity of the scattered light (the lighter the grayscale, the more intense the scattering and conversely the darker the grayscale, the less intense the scattering). The lines shown in the plots of FIG. 4 represent the polarization of the scattered light. In addition, in the plots shown in FIG. 4, the illumination is coming in from the left and going out on the right, and the illumination used is p-polarized light.

In one embodiment, configuring the polarizing element to separate the scattered light into the different portions is performed to maximize the signal-to-noise ratio detected by the detector for only a subset of the defects on the wafer. For example, plot 410 shows simulated measurements of particle scattering across the collection NA of the collection subsystem described herein and without using any polarizing element. As shown in this plot, the intensity of the scattering from the particle is stronger at higher NAs, while the polarization of the light scattered from the particle changes substantially across the collection NA. Plot 412 shows simulated measurements of surface scattering (intensity in log scale) across the collection NA of the collection subsystem described herein and without using any polarizing element. Although the intensity of the light scattered by the surface depends on the spatial frequency distribution of the surface roughness, the polarization of the surface scattering is substantially aligned across substantially large portions of the collection NA. The polarizations of both scattered light from a particle and scattered light from the surface are mirror symmetric with respect to the incident plane (which is the horizontal line through the center of the full NA shown in plots 414 and 416) when the polarization used for illumination is P, S, or other symmetric polarizations.

Plot 414 shows simulated measurements of particle scattering across the collection NA of the collection subsystem described herein when using a linear polarizer that has mirror symmetric polarizations with respect to the incident plane and that transmits light having the polarizations shown by the white tines across plot 414. Plot 416 shows simulated measurements of surface scattering across the collection NA of the collection subsystem described herein when using a linear polarizer that transmits light having the mirror symmetric polarizations shown by the white lines across plot 416. As shown by comparison of plots 414 and 416, in areas of the collection NA where particle scattering is mostly transmitted by the polarizer, the surface scattering is mostly blocked by the polarizer. Therefore, by detecting light in only those areas, the signal-to-noise ratio for the particles can be increased. In this manner, in one embodiment, the polarizing element has mirror symmetry with respect to an incident plane of the illumination subsystem, and the one of the different segments includes one or more individual segments of the collection NA in which intensity of the scattered light from particles on the wafer is highest across the entire collection NA and in which polarization of the scattered light from the wafer is substantially aligned within each of the one or more individual segments and is mirror symmetrical with respect to the incident plane such that the scattered light from the wafer can be separated within the one or more individual segments from the scattered light from the particles by the polarizing element.

For example, an optical element such as those described herein can be used to selectively detect light within the areas shown in plots 418 and 420 surrounded by the white lines (by selectively transmitting or selectively reflecting the light in the areas surrounded by the white lines depending on the configuration of the system) since as shown in plot 418, the particle scattering that would be transmitted by the polarizer in those areas is relatively intense while as shown in plot 420, the surface scattering that would be transmitted by the polarizer in those areas in not substantially intense. Therefore, the areas shown in plots 418 and 420 surrounded by the white lines represent one different segment of the collection NA that can be separated from other segments of the collection NA by the optical elements described herein. As shown in these plots, the one of the different segments includes two individual segments that are mirror symmetrical to each other about an incident plane of the illumination subsystem (represented by the horizontal white lines in plots 414 and 416). This different segment may be further configured as described herein. The optical element can be positioned in the Fourier plane or at a conjugate of the Fourier plane of the collection subsystem as described herein. For p-polarized illumination, the haze reduction is about 50× to about 100× depending on characteristics of surface roughness, and signal reduction is only about 2×. Therefore, the embodiments described herein provide a significant improvement in signal-to-noise ratio (and therefore sensitivity) over existing architectures that use full NA collection. For relatively small spot sizes, and with sufficient laser power, sensitivity is limited by speckle noise. Taking into account the higher speckle contrast due to the reduction of aperture, the overall maximum signal-to-speckle noise improvement provided by the combination of the optical element and the polarizing element for the scattering shown in FIG. 4 is about 20× over that of the full un-polarized NA.

In addition, the optical element and polarizing element combinations described herein allow detection of the particle scattering over a much larger area compared to the areas over which light is detected in currently used segmentation schemes. The larger area of collection NA allows more efficient collection of scattered light from particles, therefore minimizing the shot noise of the signal. In particular, the shot noise of the signal is proportional to the square root of the signal. Therefore, the ratio of the signal to the noise of the signal is inversely proportional to the signal. As such, the shot noise of the signal limits the capture rate of particles. Therefore, the relatively large collection area provided by the embodiments described herein not only improves the ratio of the signal to the noise of the background, but also the ratio of the signal to the noise of the signal. In contrast, the relatively small NA of collection used in currently available systems has relatively poor collection efficiency of scattering from particles. In particular, even though the ratio of the signal to the noise of the surface scattering may be relatively high (division by a substantially small number), the ratio of the signal to the noise of the signal can be substantially low, which reduces the defect capture rate. Another adverse effect of relatively small signals as a result of using relatively small collection aperture(s) is that other noise sources such as stray light and detector dark current may become dominant and limit the detection sensitivity. In this manner, as described above, in some embodiments, the optical element and the polarizing element are configured to optimize the system for detection of particles on the wafer by maximizing signal-to-noise ratio of scattering from particles detected by the detector and minimizing loss of signal corresponding to the particles due to the optical element and the polarizing element. As such, the system may include one channel that is optimized for particle sensitivity by using the optical element configuration (e.g., shape) combined with the polarization orientation to maximize the signal-to-noise ratio and to minimize the loss of signal.

Figure 5:
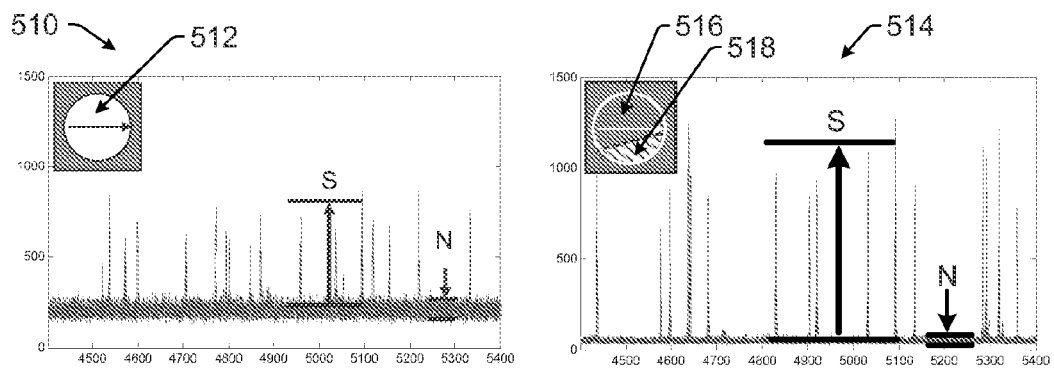
FIG. 5 includes plots showing the intensity of particle and surface scattering when detecting scattered light in one different segment of a collection NA with optimum polarization in the system embodiments described herein and without using the one different segment and the optimum polarization.

FIG. 5 shows experimental data that confirms the theoretical simulation shown in FIG. 4. For example, as shown in FIG. 5, plot 510 shows the signal, S, of scattered light due to defects on a wafer and noise, N, due to surface scattering measured for the wafer using a full collection NA, shown by reference numeral 512, of 0.95 (i.e., no optical element was used for these measurements). The illumination used was p-polarized light, and no polarizing element was positioned in the path of the light scattered from the wafer. In contrast, plot 514 shown in FIG. 5 shows the signal, S, of scattered light due to defects on the wafer and noise, N, due to surface scattering measured for the wafer using optical element 516 having side opening 518. The illumination used was p-polarized light, and a 50 degree linear polarizer (i.e., a linear polarizer with its pass axis oriented at 50 degrees) (represented by the diagonal lines shown in side opening 518) was positioned in the collection path of the light. As shown in FIG. 5, the signal-to-noise ratio detected using the optical element and linear polarizer combination is significantly higher than the signal-to-noise ratio detected using a full collection NA and no polarizing element.

Using linear polarizers in the embodiments described herein is advantageous because they are readily available with maximum reflection/transmission efficiency. For example, the efficiency of a linear polarizer may be greater than 95% compared to the efficiency (e.g., about 60%) of wire grid polarizers that are typically used as segmented polarizers. In another embodiment, the polarizing element is a linear polarizer that covers a majority of the imaging NA of the collection subsystem. For example, as described above, as a result of the Fourier transform, the polarization of surface scattering is aligned nearly parallel over a substantial portion of the collection NA in the Fourier plane, which allows the use of a linear polarizer that covers a majority of the imaging NA. As a result, the signal-to-noise ratio is dramatically improved and the system implementation is much simpler.

Figure 6A:
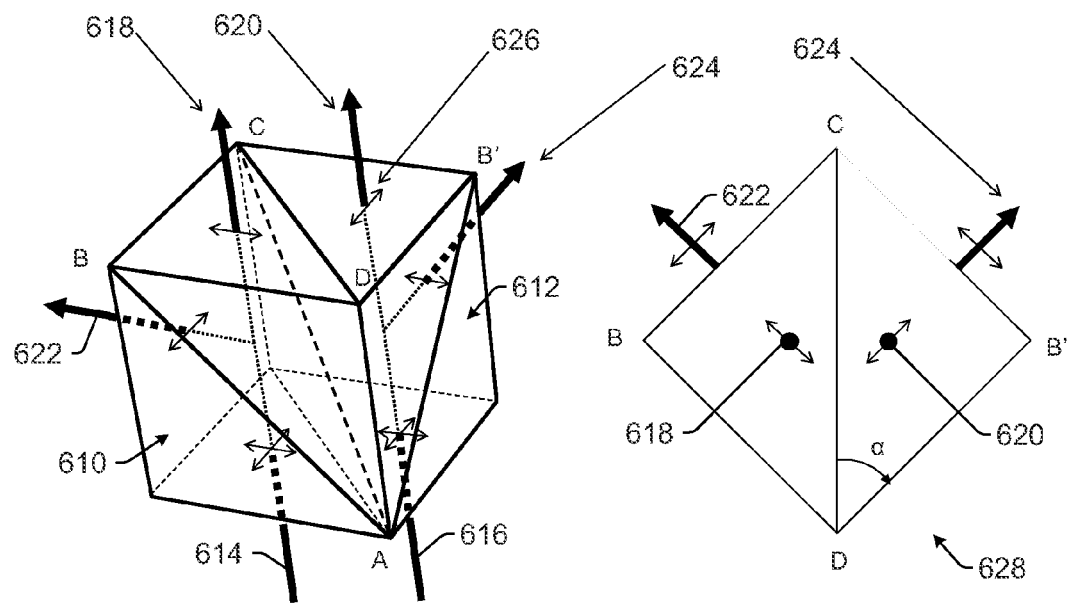
FIG. 6a is a schematic diagram illustrating a perspective view and a top view of one embodiment of a polarizing component that has mirror symmetry with respect to an incident plane of an illumination subsystem described herein.
Figure 6B:
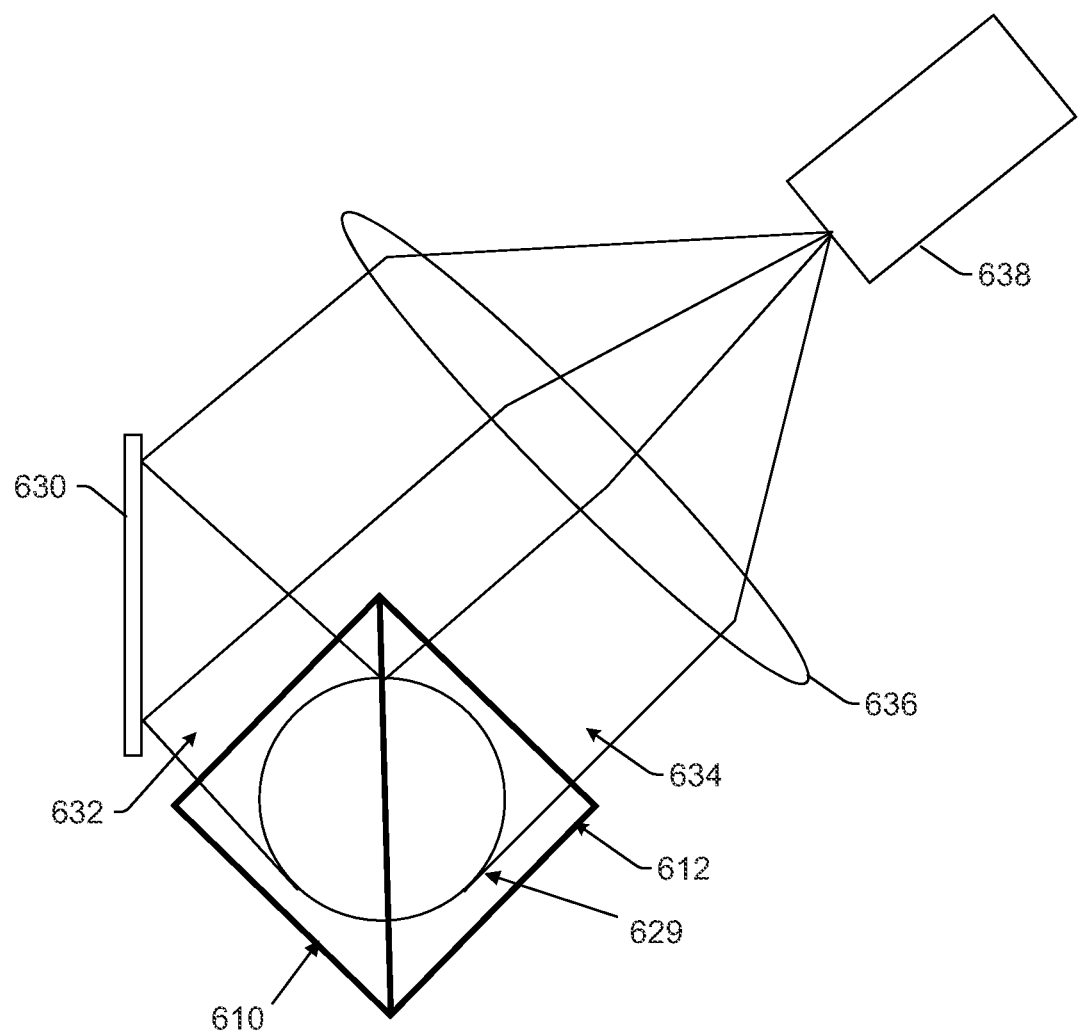
FIG. 6b is a schematic diagram illustrating a top view of one embodiment of a polarizing element that has mirror symmetry with respect to an incident plane of an illumination subsystem described herein and a folding mirror for combining two reflected beams onto one detector.

In one embodiment, the polarizing element includes two parts of two polarizing beam splitters that have been joined to each other such that the polarizing element is mirror symmetrical with respect to an incident plane of the illumination subsystem. Such a polarizing element may be configured as shown in FIGS. 6a and 6b. For example, the polarizing element may include two halves 610 and 612 of a regular polarizing beam splitter (PBS) cube. In other words, the polarizing element may be made of two regular polarizers that are cut at a proper angle and are stitched back together. For example, the polarizing element may be two separate pieces of a polarizing beam splitter that has been cut into two pieces and glued back together. Such polarizing elements can also be made of wire grid polarizers that are manufactured on a single substrate. However, any orientation of the polarizing element is possible. In this manner, the polarizing element has mirror symmetry with respect to the incident plane of the system. In addition, the linear polarizer may cover the entire aperture, having mirror symmetry with respect to the incident plane.

The corners of the polarizing component are labeled by ABB'CD for the convenience of defining relevant planes. The plane ADC may be coincident (or substantially coincident) with the incident plane of illumination of the wafer. Plane ABC is the polarizing beam splitting surface of one half of a PBS cube and AB'C is the polarizing beam splitting surface of the other half of the PBS cube, Planes ABC and AB'C intersect at the line AC and are not parallel to each other. Incoming light beams 614 and 616 (shown as two light beams in FIG. 6a for description purposes only) are separated by the polarizing element into transmitted beams 618 and 620, respectively, and reflected beams 622 and 624, respectively. All of double headed arrows 626 shown in FIG. 6a represent the polarization orientation of the light beams that the arrows intersect. The reflected light beams have S polarization, and the transmitted light beams have P polarization for both halves of the polarizing element; however, the S and P polarizations are defined with respect to the incident planes of the reflecting surfaces ABC and AB'C respectively. The incident plane for surface ABC is parallel to surface ABD, and the incident plane of surface AB'C is parallel to surface AB'D. The transmitted light and the reflected light have mirror symmetry with respect to the incident plane of wafer illumination ACD, as shown in top view 628. In the top view, α is the transmitted polarization angle with respect to the incident plane of illumination. The angle of polarization is 45 degrees for this example, but can be any angle by cutting and combining the PBS cube at the corresponding angle.

Unlike a regular PBS cube, which separates one incident beam into two beams, one transmitted beam having one polarization and one reflected beam having an orthogonal polarization, the polarizing element shown in FIG. 6a splits one incident beam into three beams: one transmitted beam having a mirror symmetric polarization and two reflected beams having mirror symmetric polarizations. The two reflected beams are not parallel to each other and propagate in different directions. In some embodiments, the two reflected beams may be separately collected and directed to two separate detectors. Output generated by the two separate detectors may be used individually or in combination for better defect detection and/or classification. However, the two reflected beams may be directed onto a single detector for simpler and more cost effective system configurations. For example, as shown in FIG. 6b, incoming beam 629 may be separated by a polarizing element, having two halves 610 and 612 that may be configured as described above, into reflected beams 632 and 634. Reflective optical element 630 may be used to fold reflected beam 632 to be parallel to reflected beam 634 so that beams 632 and 634 can be focused by lens 636 onto the same detector 638. A total internal reflection prism (not shown) may be used in place of the folding mirror shown in FIG. 6b to fold one of the reflected beams. Reflective optical element 630, lens 636, and detector 638 may include any suitable such components. Light that is transmitted by each of the sections of the polarizing element shown in FIG. 6b may also be detected by another detector (not shown in FIG. 6b), which may be configured as described further herein. There are many other ways to combine two beams into one for cost effectiveness. Another example (not shown in detail) is to introduce a half wave plate between optical element 126 and polarization element 132 in FIG. 1a to FIG. 1d. The half wave plate will be positioned in the path of only light transmitted by either transmissive portion 154 or transmissive portion 152, shown in FIGS. 1b-1d. The orientation of the half wave plate is aligned such that the polarization of the light transmitted by the two transmissive portions (152 and 154) is the same before entering polarization element 132. In this way, only one detector is needed. It is also possible to use two half wave plates (one on light transmitted by transmissive portion 152 and the other on light transmitted by transmissive portion 154). The orientation of each half wave plate is separately aligned such that polarization of light transmitted by the two transmissive portions (152 and 154) is the same before entering polarization element 132.

Figure 7:
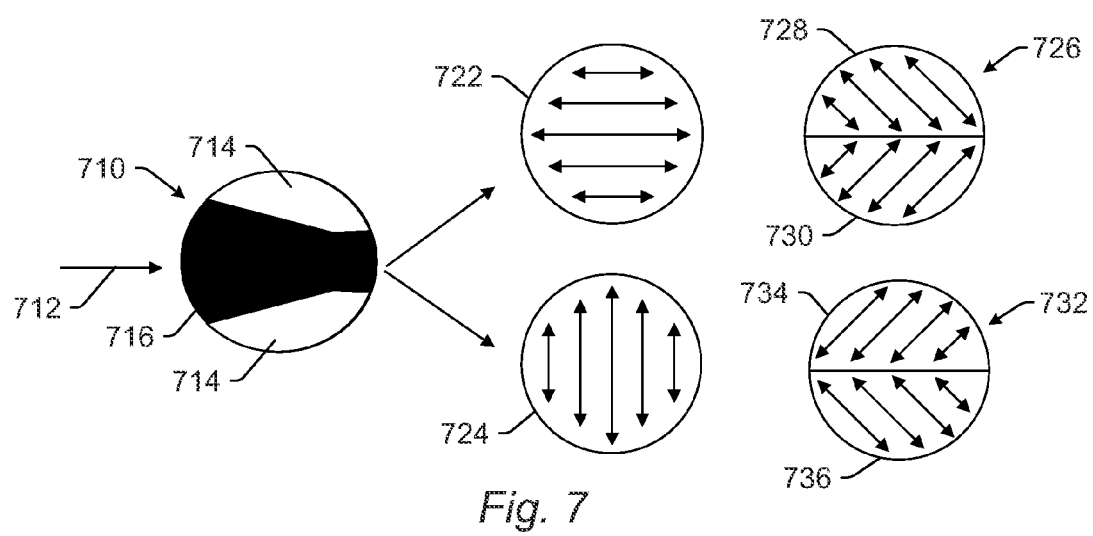
FIG. 7 is a schematic diagram illustrating cross-sectional views of one embodiment of a segment of the collection NA of the collection subsystem described herein and various ways in which a polarizing element described herein can separate the scattered light in the segment into different portions of the scattered light based on polarization.

FIG. 7 illustrates various polarizations that can be separated by various polarizing elements (not shown in FIG. 7) described herein that may be used in combination with an embodiment of an optical element (not shown in FIG. 7) described herein. For example, in FIG. 7, the direction of illumination is shown with respect to collection NA 710 by arrow 712, and the incident plane of illumination is parallel to arrow 712 and across the center of collection NA 710. Light scattered into the entire collection NA 710 can be separated by an optical element described herein into light scattered into different segments 714 and 716 that are complementary to each other. In the embodiment shown in FIG. 7, segment 714 includes two individual segments that may be further configured as described herein. The light scattered into these different segments can be separated by one of the optical elements described herein that has reflective and transmissive portions that correspond to the different segments of the collection NA shown in FIG. 7. In this manner, the optical element segments the collection NA of a collection subsystem (not shown in FIG. 7).

Various polarizing elements may be positioned in the path of the light reflected and transmitted by the optical element. For example, a linear polarizer, which transmits light having the same polarization across substantially the entire polarizing element, may be positioned in a path of the scattered light separated into one of the different segments of the collection NA by the optical element. The linear polarizer may be a single piece of polarizer, which may be used in the systems described herein in cases in which the polarization is substantially completely aligned across the entire collection NA segment corresponding to the channel in which the polarizing element is included.

Light transmitted by the linear polarizer having polarization 722 and light reflected by the polarizing element having orthogonal polarization 724 may be collected and detected as described further herein. Both transmitted and reflected light may be collected and detected such that substantially none of the scattered light separated into the different segment by the optical element is lost. For example, light transmitted by the polarizing element may be directed to one detector (not shown in FIG. 7), and light having a different, orthogonal, and mutually exclusive polarization than the light transmitted by the polarizing element may be directed to another detector (not shown in FIG. 7). In other words, the light transmitted by the polarizing element having a first polarization may be directed to a first detector, and the light reflected by the polarizing element having a second polarization, which is different than, orthogonal to, and mutually exclusive of the first polarization, may be directed to a second detector. In this manner, scattered light separated into any segment of the collection NA may be further separated into different portions having polarizations that are different, orthogonal, and mutually exclusive that may be detected by different detectors. Therefore, light in any segment of the collection NA may be separated based on polarization by a polarizing element and separately detected by different channels of the system.

The system may include mirror symmetrical polarizing element(s). For example, when a polarizing element such as that shown in FIGS. 6a and 6b is positioned in a path of the scattered light separated into one of the different segments of the collection NA, the transmitted portion of the light may have polarization orientation 726 having mirror symmetry with respect to the incident plane, while the reflected portion of the light may have polarization orientation 732 which is also mirror symmetric to the incident plane. In particular, as shown in FIG. 7, polarization 726 of the transmitted portion of the light includes two different polarizations 728 and 730, the orientation of which is shown by the double arrow lines across the portion, which are different than each other, orthogonal to each other, mutually exclusive of each other, and mirror symmetric to each other. In a similar manner, polarization 732 of the reflected portion of the light includes two different polarizations 734 and 736, the orientation of which is shown by the double arrow lines across the portion, which are different than each other, orthogonal to each other, mutually exclusive of each other, and mirror symmetric to each other. In addition, polarizations 728 and 734 correspond to the same segment of the collection NA but are orthogonal to each other, and polarizations 730 and 736 correspond to the same segment of the collection NA but are orthogonal to each other.

Light that is transmitted by the polarizing element may be collected and detected as described herein. Light that is not transmitted by the polarizing element may also be collected and detected such that substantially none of the light separated into a segment of the collection NA is lost. For example, light that is transmitted by both portions of the polarizing element may be directed to one detector (not shown in FIG. 7), and the light that is reflected by both portions of the polarizing element may be directed to another detector (not shown in FIG. 7). In this manner, light separated into a segment of the collection NA by the optical element may be separated based on polarization by a polarizing element and separately detected by different channels of the system.

The system also includes a detector configured to detect one of the different portions of the scattered light and to generate output responsive to the detected light. The output is used to detect defects on the wafer. In addition, as described above, light separated into different portions by a polarizing element described herein can be directed to and detected by different detectors or detection channels. For example, in one embodiment, the different portions of the scattered light separated based on polarization by the polarizing element have orthogonal, mutually exclusive polarizations, and the system includes another detector configured to detect another of the different portions of the scattered light. In one such example, as shown in FIG. 1a, portions 134 and 136 may be directed to detectors 138 and 140, respectively, by refractive optical elements 142 and 144, respectively. Each of the detectors is configured to detect one of the different portions of the scattered light and to generate output responsive to the scattered light.

Detector 138 may be configured to have maximum sensitivity to particles. For example, light that is transmitted by optical element 126 is transmitted by polarizing element 132, which is focused by a refractive optical element to detector 138. As such, the light that is detected by detector 138 goes straight through the collection path without being reflected by any optical element. In this manner, the system is preferably configured for avoiding any reflections (prior to passing through polarizer 132) of the light detected by detector 138 to thereby maximize transmission efficiency and to eliminate phase retardation in the light that may be caused by folding mirrors or other reflective optical elements.

In one embodiment, the optical element and the polarizing element are configured to optimize the system for detection of particles on the wafer by maximizing the signal-to-noise ratio of scattering from particles detected by the detector and minimizing loss of signal corresponding to the particles due to the optical element and the polarizing element. For example, the optimization of the shape of the different segments of the collection NA and the polarization orientation of fife polarizing component with mirror symmetric polarization represents a new concept of optimization. In particular, the shape of the segment of the collection NA transmitted by the optical element combined with the mirror symmetric polarizing element will suppress haze and minimize the loss of signal thereby improving the signal-to-noise significantly. In addition, surface scattering is reduced over a substantially large aperture versus multiple relatively small apertures as in some currently used wafer inspection systems. For example, in currently used wafer inspection systems, surface scattering can be reduced only over a relatively small aperture, because as shown in FIG. 3, when the polarization is projected onto a hemisphere, the polarization of particle scattering (wanted signal) is perpendicular to the polarization of surface scattering (unwanted noise) only over a relatively small area. In contrast, as described herein, the surface scattering can be reduced over a much larger area. As a result, the signals detected for relatively small particles are largely preserved while surface scattering is significantly reduced.

Refractive optical elements 142 and 144 may include any suitable optical elements, as phase retardation after light passes through polarizer 132 does not have substantial impact on signal-to-noise ratio. Detectors 138 and 140 may include any suitable detectors such as a charge coupled device (CCD), a time delay integration (TDI) detector, a multi-anode photomultiplier tube (PMT), a PMT, an array of PMTs, or any other suitable detector known in the art. The output generated by the detectors may include any suitable output such as signals, data, or image data.

The output is used to detect defects on the wafer. For example, the output generated by the detectors may be provided to a computer subsystem. In one such example, the system may include computer subsystem 146 that is coupled to detectors 138 and 140 (e.g., via one or more transmission media shown by the dashed lines between the computer subsystem and the detectors in FIG. 1*a*, which may include any suitable transmission media known in the art). Computer subsystem 146 may be coupled to the detectors such that the computer subsystem can receive the output generated by the detectors. The computer subsystem may be configured to use the output generated by each of the detectors to detect defects on the wafer. The computer subsystem may be configured to use the output and any suitable algorithm and/or method known in the art to detect defects on the wafer. For example, the computer subsystem may be configured to compare the output to a threshold. If the output is above the threshold, the computer subsystem may determine that a defect is present thereby detecting a defect on the wafer. In contrast, if the output is below the threshold, the computer subsystem may determine that a defect is not present thereby not detecting a defect on the wafer. The computer subsystem may also be configured to perform other defect-related functions such as defect classification.

The computer subsystem may take various forms, including a personal computer system, image computer, mainframe computer system, workstation, network appliance, Internet appliance, or other device. In general, the term "computer subsystem" may be broadly defined to encompass any device having one or more processors, which executes instructions from a memory medium. The computer subsystem may also include any suitable processor known in the art such as a parallel processor. In addition, the computer subsystem may include a computer platform with high speed processing and software, either as a standalone or a networked tool.

Figure 1B:
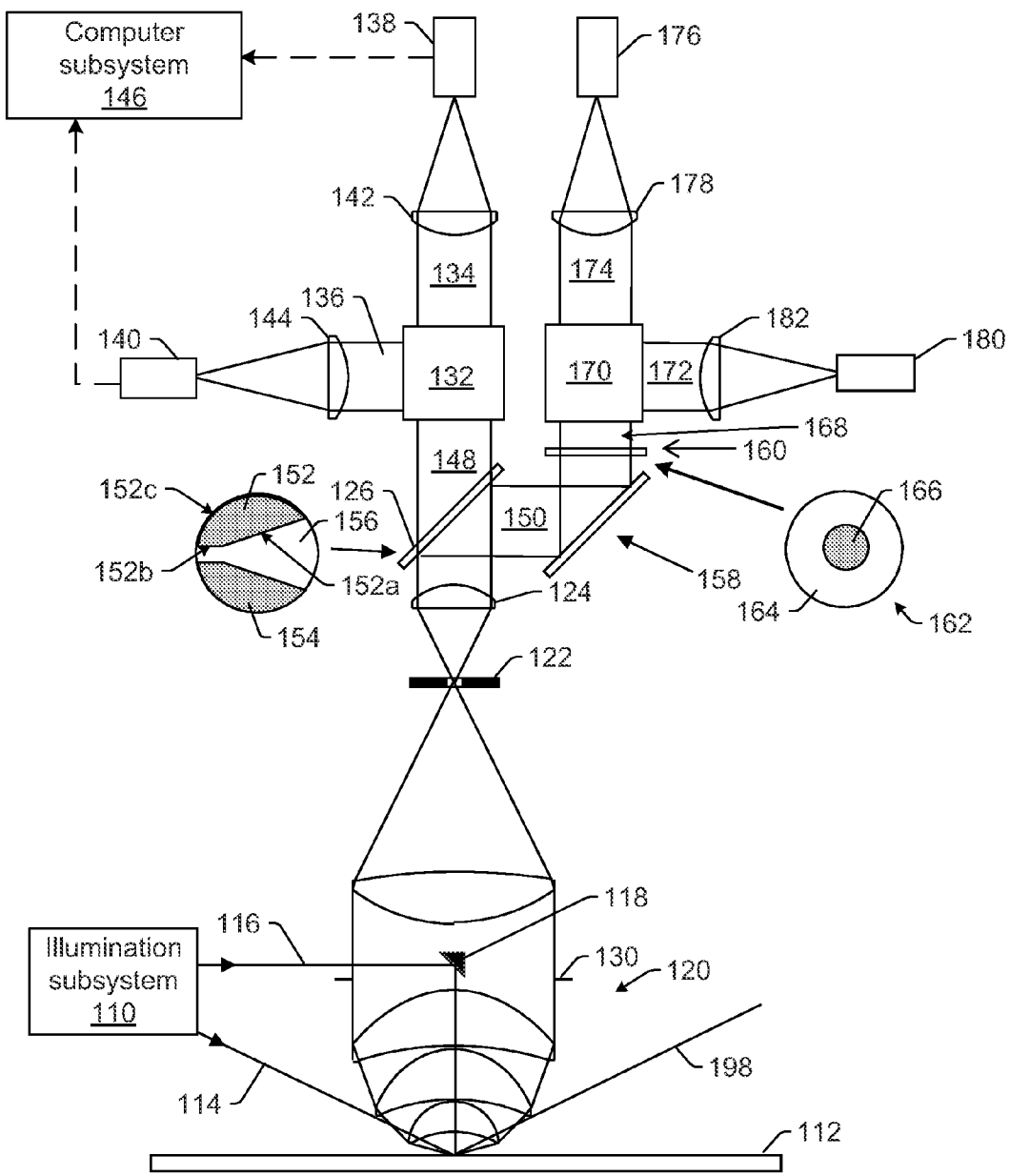

The collection NA of the collection subsystem may be segmented into multiple channels by the optical element. In one embodiment, the different segments of the collection NA are mutually exclusive. For example, as shown in FIG. 1*b*, optical element 126 may separate the scattered light collected in different segments of the collection NA into segment 148 and segment 150. Segment 148 may be transmitted by the optical element, and segment 150 may be reflected by the optical element. In this manner, the optical element may include transmissive portion(s) that correspond to one segment of the collection NA (e.g., segment 148) and reflective portion(s) that correspond to another different segment of the collection NA (e.g., segment 150). For example, as shown in cross-section in FIG. 1*b*, the optical element may include transmissive portions 152 and 154 that correspond to one segment of the collection NA and reflective portion 156 that corresponds to another different and mutually exclusive segment of the collection NA. Reflective portion 156 may reflect substantially all of the light in the segment of the collection NA corresponding to portion 156 (i.e., portion 156 may have roughly 0% transmission of the scattered light), while portions 152 and 154 may transmit substantially all of the light in the segment of the collection NA corresponding to portions 152 and 154 (i.e., portions 152 and 154 may having roughly 100% transmission of the scattered light). In this manner, the entire collection NA can be separated into two mutually exclusive portions.

As described above, the different portions of the optical element correspond to the different segments of the collection NA into which the scattered light is separated by the optical element. In addition, as shown in FIG. 1*b*, portions 152 and 154 are mirror symmetrical to each other about an incident plane of the illumination subsystem. Furthermore, as described above, portions 152 and 154 may correspond to one of the different segments of the collection NA. In this manner, one of the different segments may include two individual segments (corresponding to portions 152 and 154) that are mirror symmetrical to each other about an incident plane of the illumination subsystem. In addition, as shown in FIG. 1*b*, each of portions 152 and 154 is spaced from the incident plane. Furthermore, each of the portions can be defined by first, second, and third sides, which will be described with respect to portion 152. In particular, portion 152 includes first side 152*a*, second side 152*b*, and third side 152*c*. First side 152*a* is linear and arranged at an angle with respect to the incident plane. Second side 152*b* is linear, is substantially parallel to the incident plane, and is substantially shorter than the first side. In addition, third side 152*c* is curved. As shown in FIG. 1*b*, portion 154 is also defined by these three sides. As described above, since portions 152 and 154 correspond to one of the different segments of the collection NA, in one embodiment, one of the different segments includes two individual segments that are mirror symmetrical to each other about an incident plane of the illumination subsystem and spaced from the incident plane, each of the two individual segments has a shape defined by first, second, and third sides, the first side is linear and arranged at an angle with respect to the incident plane, the second side is linear, is substantially parallel to the incident plane, and is substantially shorter than the first side, and the third side is curved.

As can be seen by comparison of FIGS. 1b and 4, optical element 126 has characteristics (e.g., shape, relative dimensions, etc.) that are similar to the areas surrounded by the white lines shown in plots 418 and 420 except that optical element 126 is flipped over a vertical axis compared to the areas shown in plots 418 and 420. This difference in the optical element and the areas is due to the fact that FIG. 4 shows the areas as if they were in the Fourier plane of the collection subsystem, while FIG. 1b shows the configuration of optical element 126 as though it was positioned in the conjugate of the Fourier plane (since the Fourier plane and the relayed Fourier plane are substantially the same but inverted across the optical axis). Therefore, although optical element 126 is shown in FIG. 1b as being flipped compared to areas 418 and 420, optical element 126 can actually be used to separate light scattered in areas 418 and 420 of the collection NA from light scattered in other areas of the collection NA. As such, optical element 126 can be used for the optimum particle detection sensitivity as described above.

Figure 8A:
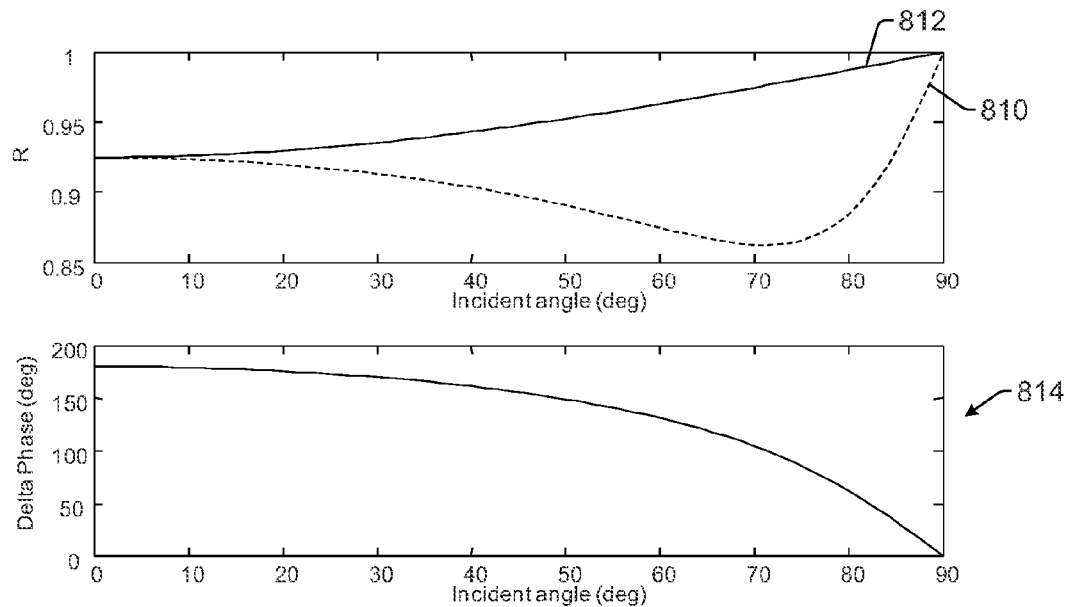
FIG. 8a includes graphs showing the reflectance change of p- and s-polarized light from a reflective optical element as a function of angle of incidence and the phase difference between the p- and s-polarized light as a function of angle of incidence.

Since the optical element shown in FIG. 1b is configured such that light scattered in one of the different segments of the collection NA is reflected by the optical element, the optical element may introduce some phase change in that scattered light. For example, line 810 shown in FIG. 8a is the reflectance of p-polarized light from an aluminum mirror as a function of incident angle, and line 812 is the reflectance of s-polarized light from the aluminum mirror as a function of incident angle. The aluminum mirror will change the phase of the light as shown by plot 814 of the phase difference as a function of angle of incidence. As such, as shown in FIG. 8a, the mirror will change the phase and amplitude between the two components of polarization and as a result will change the otherwise substantially aligned polarization of surface scattering, which makes it difficult to use a polarizer to reject the surface scattering.

Figure 8B:
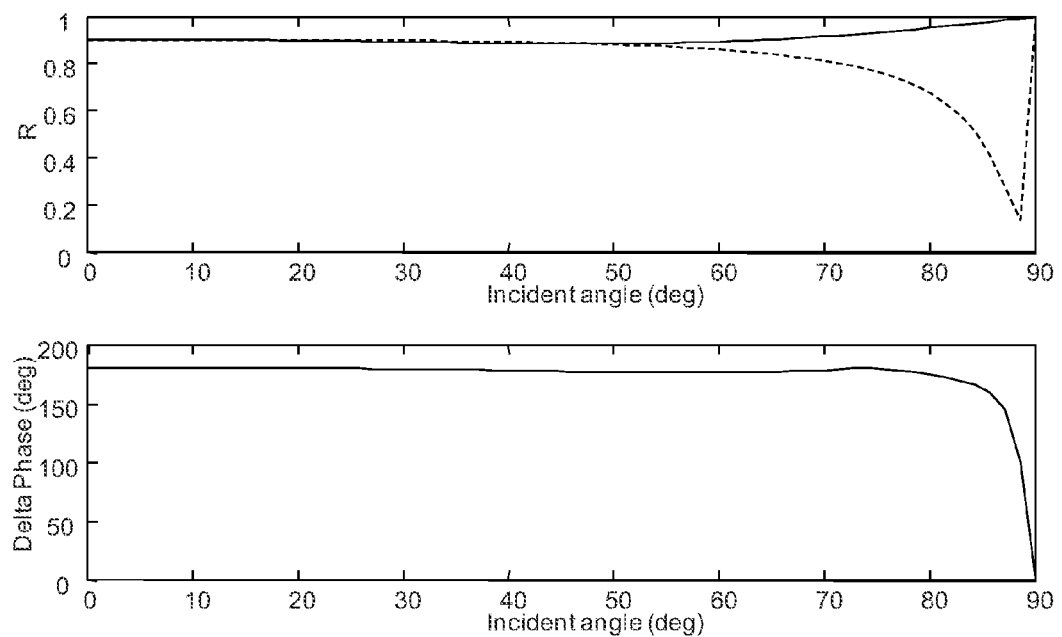
FIG. 8b includes graphs showing the reflectance and phase change of p- and s-polarized light from a reflective optical element with a thin film coating designed to generate a 180 degree phase shift over a large range of angles of incidence between P and S polarization as a function of angle of incidence.

If the light reflected or otherwise not transmitted by the optical element is not to be detected (e.g., as in the configuration shown in FIG. 1a) or is to be used for detection of defects that is not impacted by phase retardation, such phase change can be ignored. However, if the light reflected by the optical element is to be detected and used for detecting defects, then it may be advantageous to correct the phase change caused by the optical element. For example, in one embodiment, a thin film coating is formed on one or more reflective portions of the optical element, and the thin film coating is configured such that phase retardation of p- and s-polarized light caused by the one or more reflective portions is canceled upon reflection by at least one other reflective optical element of the system. In particular, a properly designed thin film coating can alter the phase between P and S polarizations reflected by a reflective optical element. For example, FIG. 8b shows the reflectance and phase retardation of an aluminum mirror coated with $MgF_2$ having a thickness of about 55 nm. The phase shift between P and S polarization is about 180 degrees over a substantially large range of incident angles. The 180 degree phase shift can be cancelled by introducing a second reflection by the same or another reflective optical element, which brings the total phase change to 360 degrees which is equivalently zero degrees. In other words, an even number of reflections can have a net phase shift of approximately zero degrees. For example, as shown in FIG. 1b, the system may include reflective optical element 158, which can be coated with the same coating described above. The reflective optical element 158 introduces another reflection of the scattered light reflected by the optical element thereby producing an even number of reflections of that light. As such, reflective optical element 158 can compensate for the phase change introduced by optical element 126 thereby making the phase change in the scattered light substantially zero. Therefore, reflective optical element 158 may provide a second reflection for a double reflection configuration that preserves the polarization of the scattered light in the reflected segment of the collection NA that may be directed to other detector(s) as described herein. In this manner, reflective optical element 158 may function as a phase compensating mirror.

In one embodiment, the system includes an additional optical element positioned in the path of the scattered light collected in another of the different segments of the collection NA, an additional polarizing element, and an additional detector. For example, the system may include additional optical element 160 positioned in the path of the scattered light collected in the segment of the collection NA that is reflected by optical element 126 (after the scattered light has been reflected by reflective optical element 158). The additional optical element is configured to separate the scattered light in the other of the different segments into additional different segments of the collection NA. For example, as shown in cross-sectional view 162, the additional optical element may include portion 164 that reflects the collected scattered light in one segment of the collection NA and portion 166 that transmits the collected scattered light in another segment of the collection NA. Like optical element 126, the different portions of additional optical element 160 may be either 0% transmissive or 100% transmissive. As such, the different segments of the collection NA into which scattered light is separated by the additional optical element may be different and mutually exclusive. In addition, the different segments of the collection NA into which scattered light is separated by the two optical elements may be different and mutually exclusive. For example, scattered light in the segment of the collection NA that is transmitted by optical element 126 cannot also be transmitted or reflected by additional optical element 160 because none of the light in that transmitted segment of the collection NA is reflected by the optical element to the additional optical element.

In this manner, the additional optical element is used to segment the collection NA into multiple channels. For example, the additional optical element may have at least one portion that reflects light and at least one other portion that transmits light. Therefore, the additional optical element may segment the collection NA into two segments, one segment of which is directed into one channel by reflection and another segment of which is directed into another channel by transmission.

The additional optical element can be configured and manufactured as described above. The additional optical element is positioned at or near the Fourier plane of the collection subsystem or at or near a conjugate of the Fourier plane. For example, one optical element may be positioned at the Fourier plane and the other optical element may be positioned at the conjugate of the Fourier plane. In another example, one optical element may be positioned at a conjugate of the Fourier plane and another optical element can be positioned near the conjugate of the Fourier plane. In this manner, the optimization performed by the additional optical element may also be performed at a Fourier plane or a conjugate of the Fourier plane versus on the surface of a hemisphere as is currently performed. The additional optical element may be further configured as described herein.

In addition, it is noted that the conjugate Fourier plane of the collection subsystem is rotated 180 degrees around the optical axis of collection with respect to the Fourier plane of the collection subsystem. Therefore, the optical element may be rotated 180 degrees around the optical axis such that the reflective and transmissive portions of the optical element align with the segments of collection NA depending on if the optical element is positioned at or near the Fourier plane or at or near the conjugate of the Fourier plane.

Scattered light 168 in one additional segment transmitted by additional optical element 160 is directed to additional polarizing element 170. The additional polarizing element is configured to separate the scattered light in one of the additional different segments into additional different portions of the scattered light based on polarization. For example, the additional polarizing element may split the polarization of collection into two orthogonal polarizations. Additional polarizing element 170 may be configured as described herein with respect to polarizing element 132. For example, additional polarizing element 170 may have mirror symmetry with respect to the incident plane of the illumination subsystem. Additional polarizing element 170 is configured to separate the scattered light in one of the additional different segments into additional different portions 172 and 174.

The additional detector is configured to detect one of the additional different portions of the scattered light and to generate output responsive to the detected light. For example, additional detector 176 is configured to detect the additional different portion of the scattered light transmitted by the additional polarizing element. In particular, portion 174 of the light may be focused by refractive optical element 178 to detector 176 such that detector 176 can detect the portion of the light transmitted by polarizing element 170 and generate output responsive to that portion of the light. Detector 176 may be coupled to computer subsystem 146 as described above such that the computer subsystem can use the output generated by detector 176 to detect defects on the wafer and/or to perform one or more other functions (e.g., defect classification) described herein. Additional polarizing element 170, refractive optical element 178, and detector 176 may be further configured as described herein.

In one such embodiment, the different segments, the additional different segments, and any other different segments of the collection NA are complementary to each other such that in combination the detector, the additional detector, and any other detectors included in the system detect light across substantially the entire collection NA of the collection subsystem. For example, the gaps between the segments of the collection NA detected by each of the channels can be minimized, Practically zero gap between NA segmentation allows maximum collection efficiency.

Figure 9:
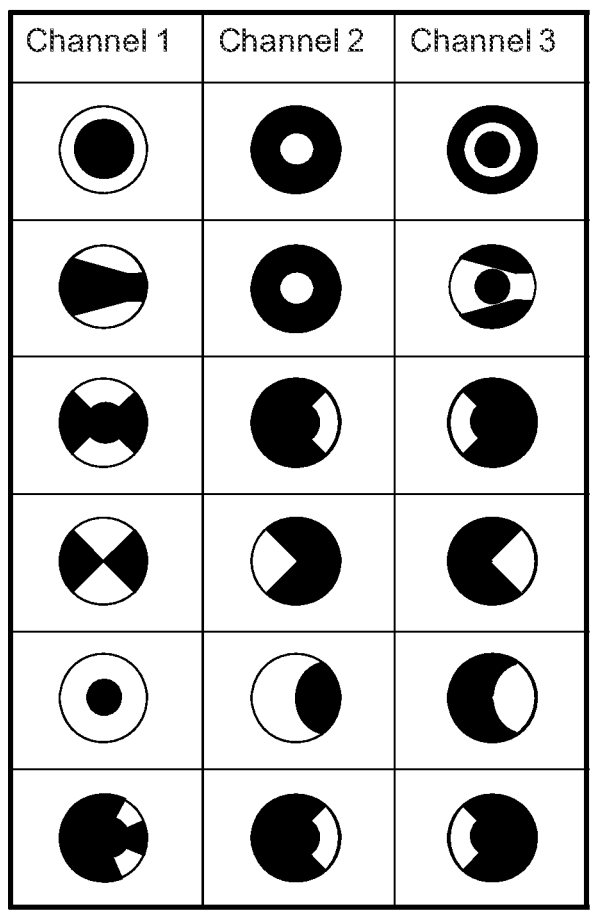
FIG. 9 is a schematic diagram illustrating various embodiments of different segments of the collection NA of the collection subsystem described herein into which collected scattered light may be separated by the embodiments described herein.

Examples of complementary segments of collection NA are shown in FIG. 9. In FIG. 9, the white area(s) represent the segment(s) of the collection NA that are collected by each channel. Each channel may or may not be further split into two orthogonal polarizations as described herein. The first column in FIG. 9 includes examples of a first segment of the collection NA that can be directed into a first channel of an inspection system. The second column in FIG. 9 includes examples of a second segment of the collection NA that can be directed into a second channel of the inspection system. The third column in FIG. 9 includes examples of a third segment of the collection NA that can be directed into a third channel of the inspection system.

Each row in FIG. 9 includes segments of the collection NA that are complementary to each other. For example, in the first row shown in FIG. 9, the first segment of the collection NA that is directed to channel 1 includes an annular region adjacent to the edge of the collection NA. The second segment of the collection NA that is directed to channel 2 includes a centermost region of the collection NA, while the third segment of the collection NA that is directed to channel 3 includes an annular region surrounding the centermost portion of the collection NA and within the annular region corresponding to channel 1. In this manner, each of the different channels detects light in a different, mutually exclusive segment of the collection NA, and the segments of the collection NA corresponding to each of the channels in combination cover substantially the entirety of the collection NA. Therefore, the three segments shown in the first row of FIG. 9 are complementary to each other. However, the segments of the collection NA may not be complementary to each other. For example, each of the segments of the collection NA is preferably optimized for one type of defects. Therefore, the optimum segments may not be complementary segments. In addition, gaps between the segments may be allowed.

In another such embodiment, the additional different portions of the light have orthogonal, mutually exclusive polarizations, and the system includes another additional detector configured to detect another of the additional different portions of the scattered light. For example, referring back to FIG. 1*b*, polarizing element 170 may also reflect a portion of the light transmitted by optical element 160. The light reflected by the polarizing element my be directed to another detector 180 such that this portion of the light can also be detected. For example, the portion of the light reflected by polarizing element 170 may be focused by refractive optical element 182 to detector 180 such that detector 180 can detect the portion of the light reflected by polarizing element 170 and generate output responsive to that portion of the light. Detector 180 may be coupled to computer subsystem 146 as described above such that the computer subsystem can use the output generated by detector 180 to detect defects on the wafer and/or to perform one or more other functions (e.g., defect classification) described herein. Refractive optical element 182 and detector 180 may be further configured as described herein. In this manner, scattered light having different, orthogonal, and mutually exclusive polarizations may be separated by polarizing element 170 and separately detected by detectors 176 and 180.

In this manner, the system may include four independent channels of collection: two complementary segments of collection NA (defined by the optical elements) and two orthogonal polarizations for each NA segment (defined by the polarizing element coupled to each optical element). In other words, with the relatively large collection NA of the collection subsystem, the optical elements segment the collection NA and then the polarizing elements split the two independent components of the polarization of light collected from the segmented collection NA. Obviously other combinations are also possible. For example, there can be three or more complementary segments of the collection NA. In addition, the segmentation of the collection NA may not be complementary but gaps may be allowed or configured between the different segments of the collection NA (e.g., if the highest sensitivity for a type of defects requires doing so).

In some instances, light in one of the different segments of the collection NA may be directed to another optical element that is complementary to both of the first two optical elements. For example, if optical element 160 shown in FIG. 1*b* is configured to reflect light scattered in a segment of the collection NA, a third optical element may be configured to separate the scattered light collected in the segment of the collection NA reflected by optical element 160 into further different segment(s) that can be directed to different polarizing element(s) such as any of the polarizing elements described herein. Such an optical element may be further configured as described herein.

Figure 1C:
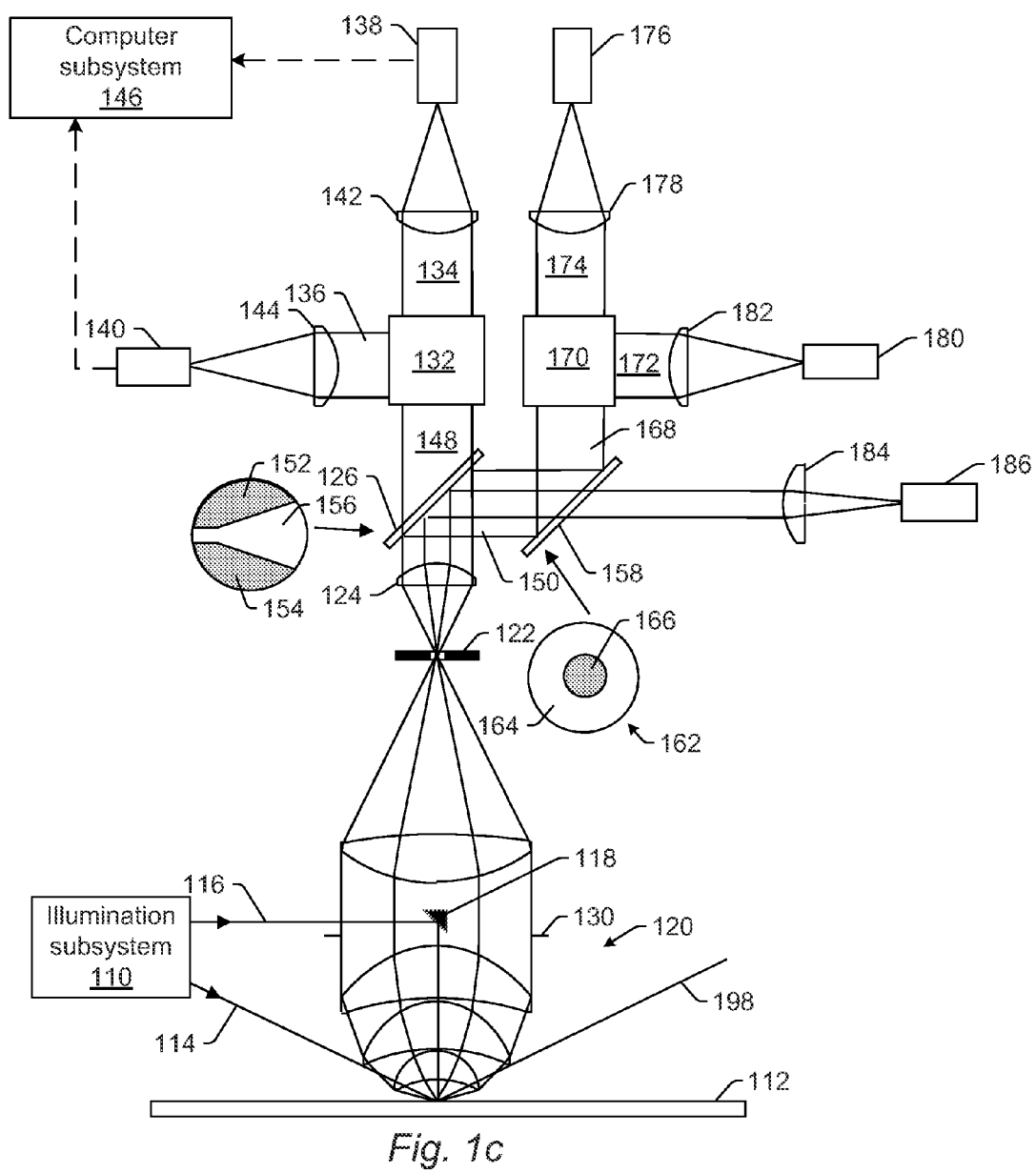

However, the third collection channel may not include an optical element and can be configured such that all of the scattered light separated into one of the different segments of the collection NA by one of the two first optical elements is detected by the third collection channel. For example, as shown in FIG. 1c, light that is reflected by optical element 126 and transmitted by optical element 158 may be directed to one or more additional channels of the inspection system. In particular, scattered light collected in the segment of the collection NA that is transmitted by optical element 158 in FIG. 1c may be directed to refractive optical element 184, which may be configured as described herein and may be configured to focus the light in that segment of the collection NA to detector 186, which may also be configured as described herein.

As shown in FIG. 1c, although optical element 126 reflects the light scattered in one different segment, which may be detected and used for defect detection, the scattered light detected by detector 186 is transmitted by reflective optical element 158, which is not compensated for the phase change that may be introduced by reflective portion(s) of optical element 126. For some segments of collection NA the phase compensation may not be required, However, the configuration of the system shown in FIG. 1c may be altered to include another reflective optical element that can be used to compensate for any phase change introduced by reflective portion(s) of optical element 126. Such a reflective optical element may be configured as described herein. The system configuration shown in FIG. 1c may be further configured as described herein.

Figure 1D:
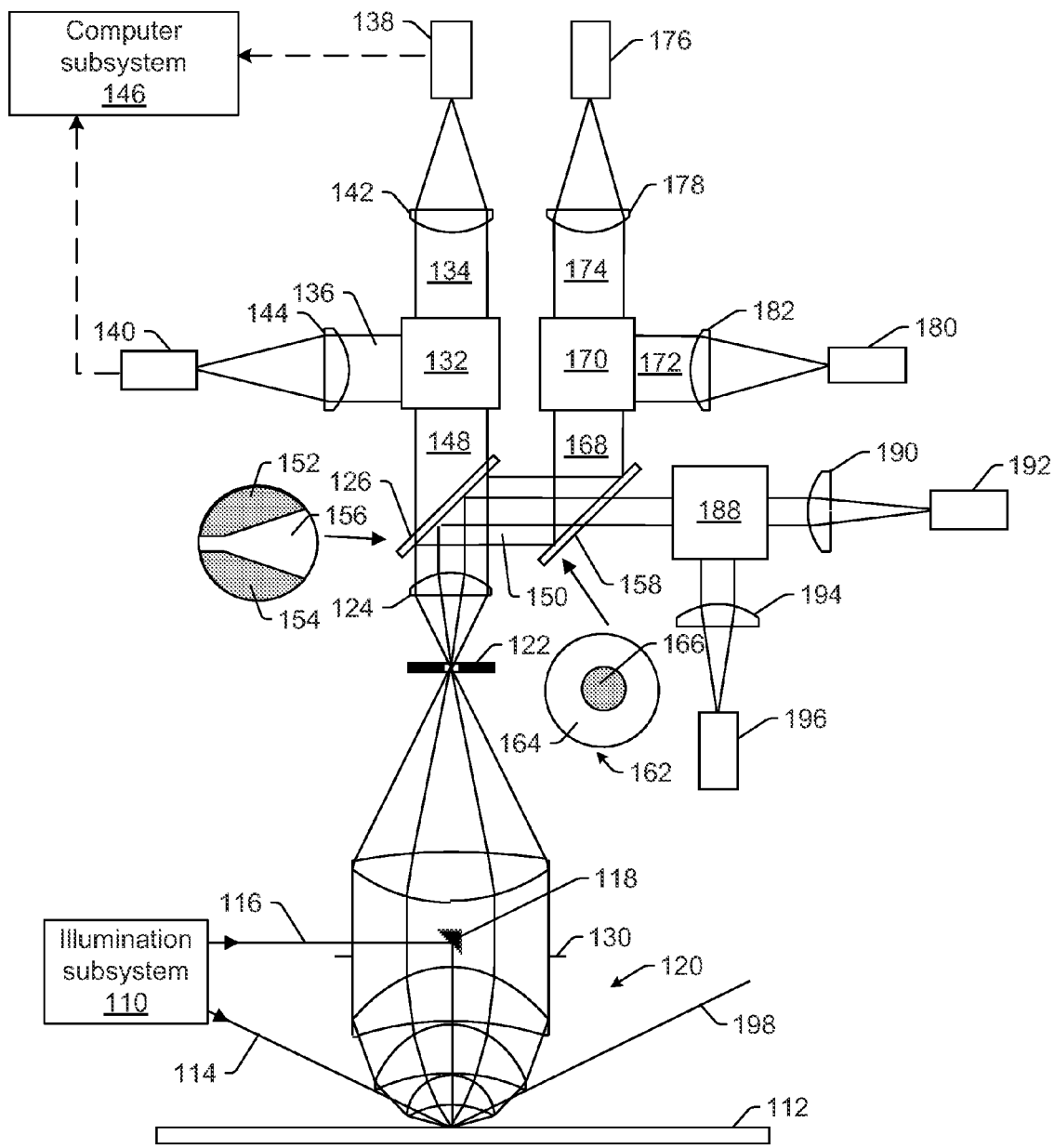

In another embodiment, the third collection channel may include a polarizing element that splits the light based on polarization into two channels. For example, as shown in FIG. 1d, light that is reflected by optical element 126 and then is transmitted by optical element 158 may be directed to one or more additional channels of the inspection system. In particular, light reflected by optical element 126 and then transmitted by optical element 158 may be directed to polarizing element 188. As shown in FIG. 1d, light directed to polarizing element 188 is only reflected once (by optical element 126); therefore, any phase retardation caused by this reflection is not compensated for by a second reflection. In this manner, the light directed to the polarizing element may be used for detection of defects that is not impacted by phase retardation. However, the system configuration shown in FIG. 1d may be altered as described further herein to include a reflective optical element (not shown) positioned in the path of the scattered light between optical element 158 and polarizing element 188 that is configured to compensate for any phase retardation in the scattered light caused by reflection of the light by optical element 126. Such a reflective optical element may be further configured as described herein. Therefore, in system configurations described herein, if required or otherwise desired, the light detected by each channel of the system may have zero phase change due to reflection by any and all optical elements included in the system.

Polarizing element 188 may be configured to separate the scattered light in one of the different segments into different portions of the scattered light based on polarization. Polarizing element 188 may include any of the polarizing elements described herein. For example, polarizing element 188 may have mirror symmetry with respect to the plane of incidence. In addition, light transmitted by polarizing element 188 may be directed to refractive optical element 190, which may include any suitable refractive optical element. Refractive optical element 190 may focus the light to detector 192, which my be configured as described herein. Light reflected by polarizing element 188 may be directed to refractive optical element 194, which may include any suitable refractive optical element and which directs the light to detector 196, which may be configured as described herein. Detectors 1192 and 196 may be coupled to computer subsystem 146 as described herein such that output generated by the detectors can be used by the computer subsystem to detect defects on the wafer and/or to perform one or more other functions described herein (e.g., defect classification). In this manner, detectors 192 and 196 may detect light scattered into a third segment of the collection NA and may separately detect the light based on polarization. Therefore, detectors 192 and 196 and their associated optics may form additional channels of the inspection system that are independent of all of the other channels of the inspection system described above. The configuration of the system shown in FIG. 1d may be further configured as described herein.

The embodiments of the system described herein may also include a bright field (BF) channel. For example, the system may include one or more refractive and/or reflective optical elements (not shown) that are configured to collect light 198 shown in FIGS. 1a-1d specularly reflected from the wafer. The refractive and/or reflective optical element(s) may include any suitable such elements known in the art. The system may also include one or more detectors (not shown) that are coupled to the refractive and/or reflective optical element(s) and that are configured to detect the light specularly reflected from the wafer. The detector(s) may include any suitable detector(s) and may be coupled to the computer subsystem as described herein such that the computer subsystem can use output generated by the detector(s) to detect defects on the wafer or to perform one or more other functions (e.g., wafer height adjustment, defect classification, etc.). For example, such light may be detected and used for determining the position of the wafer with respect to the collection subsystem and for auto-focusing of the inspection system. In one such example, output responsive to the specularly reflected light may be used by a computer subsystem described herein to alter a position of one or more optical elements of the system.

In one embodiment, the collection subsystem includes a reflective optical element. In one such embodiment, the system includes an additional reflective optical element positioned in a path of the scattered light between the reflective optical element and the polarizing element, and the reflective optical element and the additional reflective optical element are configured to in combination cause approximately zero phase change in the scattered light that is p-polarized and the scattered light that is s-polarized. For example, the reflective optical element included in the collection subsystem may be an ellipsoidal mirror, a paraboloidal mirror, a folding mirror, or any other suitable reflective optical element. In this manner, the reflective optical element may cause a phase change such as that described further herein. Such a reflective optical element may be further configured as described herein. For instance, the reflective optical element may have a thin film coating such as those described herein formed thereon. The additional reflective optical element may also include any suitable reflective optical element such as a folding mirror. The additional reflective optical element may be further configured as described herein (e.g., with a thin film coating such as that described herein) such that the additional reflective optical element can compensate for any phase retardation in the scattered light caused by reflection of the light by the reflective optical element of the collection subsystem. Therefore, in system configurations described herein, if required or otherwise desired, the light detected by each channel of the system may have zero phase change due to reflection by any and all optical elements included in the collection subsystem. In addition, the additional reflective optical element may be used in the case in which the collection subsystem includes an odd number of reflective optical elements and/or the collection subsystem reflects the collected scattered light an odd number of times.

Figure 10:
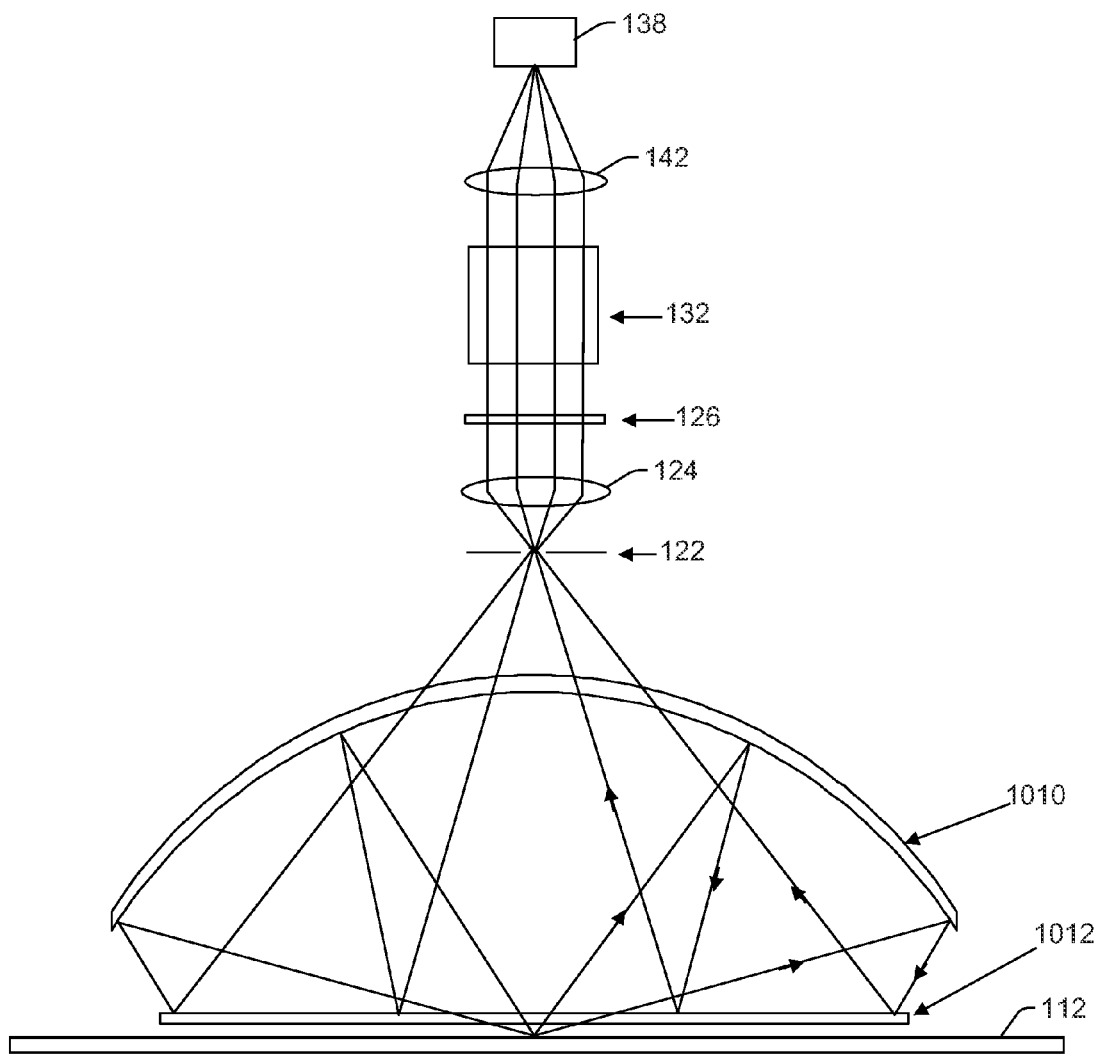
FIG. 10 is a schematic diagram illustrating a cross-sectional view of one embodiment of a reflective collector that may be included in the system embodiments described herein.

However, in other instances, the collection subsystem in of itself may be configured to reflect the light and to compensate for any phase retardation in the scattered light that is caused by the reflection of the light. For example, the collection subsystem may include an even number of reflective optical elements that are configured to reflect the scattered light an even number of times and are configured such that the overall phase change in the scattered light caused by the reflective optical elements is substantially zero. In one embodiment, the collection subsystem includes a reflective collector configured to collect the light scattered from the wafer. The reflective collector is configured to reflect the scattered light an even number of times, reflective elements of the reflective collector have thin film coatings formed thereon, and the thin film coatings are configured such that phase retardation of p- and s-polarized scattered light caused by the reflective elements is canceled upon the even number of reflections. One example of such an embodiment is shown in FIG. 10. For example, as shown in FIG. 10, the collection subsystem may include an even number (2) of reflective optical elements (reflective optical elements 1010 and 1012). Reflective optical element 1010 is configured to collect the light scattered from the wafer and to reflect the collected scattered light to reflective optical element 1012. Reflective optical element 1012 is configured to reflect the collected scattered light through field stop 122 to relay optics 124. Other elements shown in FIG. 10 may be configured as described herein. Reflective optical elements 1010 and 1012 may include any suitable reflective optical elements. As shown in FIG. 10, reflective optical elements 1010 and 1012 are configured such that the reflective collector is configured to reflect the scattered light an even number of times (twice). In addition, each of reflective optical elements 1010 and 1012 may have a thin film coating such as that described further herein formed thereon. In addition, as described herein, the thin film coatings may be configured such that phase retardation of p- and s-polarized scattered light caused by reflective optical elements 1010 and 1012 is canceled upon the even number of reflections. In this manner, the system configurations described herein may include a mirror collector with an even number of reflections (e.g., two reflective surfaces in a double mirror design) that also preserves the polarization of the scattered light (by having thin film coatings formed on the reflective surfaces that cancel the polarization phase retardation when there are an even number (2 in this design example) of reflections). The system configuration shown in FIG. 10 may be further configured as described herein. For example, although only one channel is shown in FIG. 10 for simplicity, the system configuration can include any of the multiple channel configurations described herein and shown in FIGS. 1a-1d.

In another embodiment, the system may include a mirror-based collection subsystem that in of itself does not correct for phase shift caused by the mirror-based collection subsystem. For example, the collection subsystem may include a reflective collector configured to collect the light scattered from the wafer. Such a reflective collector may include the reflective optical elements shown in FIG. 10. However, in this embodiment, the reflective collector causes a phase shift between p-polarized scattered light and s-polarized scattered light. For example, although the reflective collector reflects the scattered light an even number of times (twice), both of the reflective optical elements may not include a thin film coating such as that described herein formed thereon and therefore in combination may cause a phase shift in the scattered light. In this manner, the system may include a reflective optical element positioned in an optical path of the scattered light between the reflective collector and the polarizing element and configured to cause a phase shift between the p-polarized scattered light and the s-polarized scattered light that cancels the phase shift caused by the reflective collector such that overall phase change in the p-polarized scattered light and the s-polarized scattered light is approximately zero. For example, the system configuration shown in FIG. 10 may include a reflective optical element (such as reflective optical element 158 shown in FIG. 1b) positioned somewhere in the path of the scattered light between reflective optical elements 1010 and 1012 and polarizing element 132 shown in FIG. 10. The reflective optical element may be configured as described further herein to compensate for the phase shift caused by the reflective collector such that the overall phase change in the p-polarized scattered light and the s-polarized scattered light is approximately zero.

In one embodiment, the system includes a computer subsystem (e.g., computer subsystem 146 shown in FIGS. 1a-1d) configured to use the output generated by the detector and output generated by at least one other detector included in the system to classify the defects detected on the wafer. For example, segmenting the collection NA into multiple channels as described above can improve defect classification. In particular, different types of defects may scatter light into different segments of the collection NA differently. For example, a first type of a defect may scatter light strongly into a first segment of the collection NA and may not scatter light strongly into a second segment of the collection NA while a second type of a defect may scatter light strongly into the second segment of the collection NA and may not scatter light strongly into the first segment of the collection NA. The segments of the collection NA into which different types of defects strongly or weakly scatter light may be determined in any suitable manner (e.g., experimentally or theoretically (e.g., based on simulation)). Therefore, the segmentation of the collection NA by the optical elements may be designed based on the types of defects that will be detected by the system. In addition, the intensity or some other characteristic of the light scattered into multiple channels of the systems described herein may be used collectively (i.e., in combination) to classify defects into one of multiple types of defects.

In another embodiment, configuring the optical element to separate the scattered light collected in the different segments of the collection NA optimizes the system for detection of at least one type of defect. Configuring the optical element in this manner may also or alternatively suppress detection of at least one other type of defect. For example, segmenting the NA into multiple channels as described above can improve capturing different defect types. In particular, different types of defects may scatter light into different segments of the collection NA differently as described above. The segments of the collection NA into which different types of defects strongly or weakly scatter light may be determined in any suitable manner (e.g., experimentally or theoretically (e.g., based on simulation)). Therefore, the optical elements may be designed to segment the collection NA based on the types of defects that will be detected by the system (e.g., to direct a substantial amount of scattered light due to one type of defect to a detector of the system white not directing a substantial amount of scattered light due to another type of defect to any detectors of the system).

In one embodiment, the system includes relay optics configured to relay light from the Fourier plane of the collection subsystem to the conjugate of the Fourier plane and to control a size of the conjugate of the Fourier plane. For example, relay optics may be used to reduce the pupil (Fourier plane) size such that changing the optical elements can be more easily implemented with a slider or rotation wheel. In one such example, the relay optics (e.g., relay optics 124 shown in FIGS. 1a-1d) may be used to reduce the pupil size to roughly one or two inches in diameter. However, the relayed Fourier plane may be larger than the actual Fourier plane if the scattered light collector is substantially small. In general, the size of the relayed Fourier plane may be optimized to accommodate typical optical element sizes and/or to minimize the relative gap between segments of the collection NA. The relay optics may include any suitable refractive optical elements such as a tube lens, a relay lens, a collimating lens, a focusing lens, a condenser lens, or some combination thereof. Additional relay optics may be used to provide more than one accessible conjugate plane of the Fourier plane, so that more than one optical element can be placed at different conjugate Fourier planes when it is difficult to place the optical elements at one conjugate Fourier plane.

The segmentation of collection NA described herein is configurable, for example, by installing a set of predefined optical elements on a rotating wheel or a linear slide. In this manner, changing the optical element can be controlled by software and/or a computer, which can be part of the recipe setup process (e.g., depending on what wafers are to be inspected). For example, in another embodiment, the system includes a computer subsystem (e.g., computer subsystem 146) configured to select one of multiple optical elements included in the system to be positioned at the Fourier plane or the conjugate of the Fourier plane of the collection subsystem and to control one or more elements of the system to move the selected optical element into position in the Fourier plane or the conjugate of the Fourier plane. In this manner, segmentation is flexible and the NA can be arbitrarily divided into two, three, or more channels. As such, the system embodiments described herein provide flexible and efficient NA segmentation. The one or more elements that are controlled by the computer subsystem to effectuate changing of the optical elements may include a slider, a rotation wheel, or any other suitable mechanical and/or robotic device.

In some embodiments, the system is configured to scan light across the wafer by simultaneously rotating and translating the wafer. For example, the system may be configured to scan the light over the wafer by controlling the position of a stage (not shown) on which the wafer is disposed during inspection. The stage may include any suitable mechanical and/or robotic assembly known in the art. In such embodiments, the spot(s) illuminated on the wafer by the illumination subsystem may be stationary and only the wafer may be moved. In other words, the illumination subsystem may not be configured to scan the spot(s) over the wafer to illuminate the wafer. However, in other embodiments, the illumination subsystem may be configured to move the spot(s) over the wafer surface to thereby scan the wafer. For example, the illumination subsystem may include any suitable optical element(s) such as an acousto-optical device (AOD) or reflective optical elements such as a mirror that can be controlled (e.g., by a computer subsystem such as that described herein to scan the light over the wafer in any suitable manner (e.g., by dithering).

It is noted that the figures are provided herein to generally illustrate configurations for the system embodiments described herein. Obviously, the system configurations described herein may be altered to optimize the performance of the inspection system as is normally performed when designing a commercial inspection system. In addition, the systems described herein may be implemented using an existing inspection system (e.g., by modifying an existing inspection system based on the embodiments described herein). Alternatively, the systems described herein may be designed "from scratch" to provide a completely new system.

In some embodiments, the systems described herein may be configured as a "stand alone tool" or a tool that is not physically coupled to a process tool. However, such a system may be coupled to the process tool by a transmission medium, which may include wired and wireless portions. The process tool may include any process tool known in the art such as a lithography tool, an etch tool, a deposition tool, a polishing tool, a plating tool, a cleaning tool, or an ion implantation tool. The process tool may be configured as a "cluster tool," or a number of process modules coupled by a common handler.

Another embodiment relates to a method for inspecting a wafer. The method includes illuminating the wafer, which may be performed as described herein using any of the illumination subsystems described herein. The method also includes collecting light scattered from the wafer using a collection subsystem, which may be performed as described further herein. The collection subsystem is configured to preserve the polarization of the scattered light. The collection subsystem may be further configured as described herein. The method further includes separating the scattered light collected in different segments of the collection NA of the collection subsystem using an optical element, which may be performed as described further herein. The optical element is positioned at a Fourier plane or a conjugate of the Fourier plane of the collection subsystem. The optical element may be further configured as described herein. In addition, the method includes separating the scattered light in one of the different segments into different portions of the scattered light based on polarization using a polarizing element, which may be performed as described further herein. The polarizing element may be configured as described herein. The method also includes detecting one of the different portions of the scattered light to generate output responsive to the detected light, which may be performed as described herein. The method further includes detecting defects on the wafer using the output. Detecting defects on the wafer using the output may be performed as described further herein.

In one embodiment, the optical element and the polarizing element are configured to optimize detection of particles on the wafer by maximizing the signal-to-noise ratio of scattering from particles detected in the detecting step and minimizing loss of signal corresponding to the particles detected in the detecting step due to the optical element and the polarizing element. The optical element and the polarizing element may be further configured in this manner as described further herein. In another embodiment, the method includes configuring the optical element to separate the scattered light collected in the different segments of the collection NA to optimize the method for detection of at least one type of defect and configuring the polarizing element to separate the scattered light into the different portions to maximize the signal-to-noise ratio detected by the detecting step for only a subset of the defects on the wafer. The optical element and the polarizing element may be configured in this manner as described further herein. In an additional embodiment, the method includes using a field stop positioned in the path of the collected light to reject light scattered from air molecules near a surface of the wafer in one or more paths of one or more light beams used for illuminating the wafer. The field stop may be further configured as described herein. In a further embodiment, the polarizing element has mirror symmetry with respect to an incident plane of the illuminating step. Such a polarizing element may be further configured as described herein.

Each of the methods described above may include any other step(s) that can be performed by any of the embodiments described herein. In addition, each of the methods described above may be performed by any of the system embodiments described herein.

The results of inspection performed by the embodiments described herein may be used to alter a parameter of a process or a process tool using a feedback control technique, a feedforward control technique, or an in situ control technique. The parameter of the process or the process tool may be altered manually or automatically.

Further modifications and alternative embodiments of various aspects of the invention may be apparent to those skilled in the art in view of this description. For example, systems and methods for inspecting a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to inspect a wafer, comprising:
   an illumination subsystem configured to illuminate the wafer;
   a collection subsystem configured to collect light scattered from the wafer and to preserve the polarization of the scattered light;
   an optical element configured to separate the scattered light collected in different segments of the collection numerical aperture of the collection subsystem, wherein the optical element is positioned at a Fourier plane or a conjugate of the Fourier plane of the collection subsystem;
   a polarizing element configured to separate the scattered light in one of the different segments into different portions of the scattered light based on polarization; and
   a detector configured to detect one of the different portions of the scattered light and to generate output responsive to the detected light, wherein the output is used to detect defects on the wafer.

2. The system of claim 1, wherein the illumination subsystem is further configured to simultaneously illuminate an array of spaced apart spots on the wafer.

3. The system of claim 2, wherein the spots are spaced apart on the wafer such that adjacent spots in the array scan tracks on the wafer that are spaced apart by more than a width of the tracks.

4. The system of claim 1, wherein the illumination subsystem is further configured to illuminate the wafer by directing only p-polarized light to the wafer.

5. The system of claim 1, wherein the illumination subsystem is further configured to illuminate the wafer by directing only s-polarized light to the wafer.

6. The system of claim 1, wherein the illumination subsystem is further configured to illuminate the wafer by directing light to the wafer, and wherein the light has a polarization that is selected based on one or more characteristics of the wafer.

7. The system of claim 1, wherein the different segments of the collection numerical aperture are mutually exclusive.

8. The system of claim 1, wherein the collection subsystem comprises a. scattered light collector having a numerical aperture greater than 0.9.

9. The system of claim 1, wherein the collection subsystem comprises only one scattered light collector.

10. The system of claim 1, wherein the collection subsystem comprises only one scattered light collector configured to collect light scattered across substantially the entire scattering hemisphere of the collection subsystem.

11. The system of claim 1, wherein the system further comprises only one collection subsystem configured to collect light scattered from the wafer.

12. The system of claim 1, wherein the collection subsystem comprises a lens collector configured to collect the light scattered from the wafer, wherein the collection subsystem does not include any reflective optical elements, and wherein the collection subsystem does not alter the polarization of the scattered light.

13. The system of claim 1, wherein the collection subsystem comprises a reflective optical element, wherein the system further comprises an additional reflective optical element positioned in a path of the scattered light between the reflective optical element and the polarizing element, and wherein the reflective optical element and the additional reflective optical element are configured to in combination cause approximately zero phase change in the scattered light that is p-polarized and the scattered light that is s-polarized.

14. The system of claim 1, wherein the collection subsystem comprises a reflective collector configured to collect the light scattered from the wafer, wherein the reflective collector is further configured to reflect the scattered light an even number of times, wherein reflective elements of the reflective collector have a thin film coating formed thereon, and wherein the thin film coatings are configured such that phase retardation of p- and s-polarized scattered light caused by the reflective elements is canceled upon the even number of reflections.

15. The system of claim 1, wherein the collection subsystem comprises a reflective collector configured to collect the light scattered from the wafer, wherein the reflective collector causes a phase shift between p-polarized scattered light and s-polarized scattered light, and wherein the system further comprises a reflective optical element positioned in an optical path of the scattered light between the reflective collector and the polarizing element and configured to cause a phase shift between the p-polarized scattered light and the s-polarized scattered light that cancels the phase shift caused by the reflective collector such that the overall phase change in the p-polarized scattered light and the s-polarized scattered light is approximately zero.

16. The system of claim 1, wherein the scattered light is mapped onto the Fourier plane using vector Fourier transformation.

17. The system of claim 1, wherein the polarization of the collected light due to surface scattering from the wafer is substantially parallel across a substantial portion of the Fourier plane or the conjugate of the Fourier plane.

18. The system of claim 1, wherein a thin film coating is formed on one or more reflective portions of the optical element, and wherein the thin film coating is configured such that phase retardation of p- and s-polarized light caused by the one or more reflective portions is canceled upon reflection by at least one other reflective optical element of the system.

19. The system of claim 1, wherein the polarizing element is a linear polarizer.

20. The system of claim 1, wherein the polarizing element is a linear polarizer that covers a majority of the imaging numerical aperture of the collection subsystem.

21. The system of claim 1, wherein the polarizing element is a polarizing beam splitter.

22. The system of claim 1, wherein the polarizing element has mirror symmetry with respect to an incident plane of the illumination subsystem.

23. The system of claim 1, wherein the polarizing element comprises two parts of two polarizing beam splitters that have been joined to each other such that the polarizing element is mirror symmetrical with respect to an incident plane of the illumination subsystem.

24. The system of claim 1, wherein the different portions of the scattered light separated based on polarization by the polarizing element have orthogonal, mutually exclusive polarizations, and wherein the system further comprises another detector configured to detect another of the different portions of the scattered light.

25. The system of claim 1, wherein the optical element and the polarizing element are further configured to optimize the system for detection of particles on the wafer by maximizing signal-to-noise ratio of scattering from particles detected by the detector and minimizing loss of signal corresponding to the particles due to the optical element and the polarizing element.

26. The system of claim 1, wherein the one of the different segments comprises two individual segments that are mirror symmetrical to each other about an incident plane of the illumination subsystem.

27. The system of claim 1, wherein the one of the different segments comprises two individual segments that are mirror symmetrical to each other about an incident plane of the illumination subsystem and spaced from the incident plane, wherein each of the two individual segments has a shape defined by first, second, and third sides, wherein the first side is linear and arranged at an angle with respect to the incident plane, wherein the second side is linear, is substantially parallel to the incident plane, and is substantially shorter than the first side, and wherein the third side is curved.

28. The system of claim 1, wherein the polarizing element has mirror symmetry with respect to an incident plane of the illumination subsystem, and wherein the one of the different segments comprises one or more individual segments of the collection numerical aperture in which intensity of the scattered light from particles on the wafer is highest across the entire collection numerical aperture and in which polarization of the scattered light from the wafer is substantially aligned within each of the one or more individual segments and is mirror symmetrical with respect to the incident plane such that the scattered light from the wafer can be separated within the one or more individual segments from the scattered light from the particles by the polarizing element.

29. The system of claim 1, further comprising an additional optical element positioned in the path of the scattered light collected in another of the different segments of the collection numerical aperture, an additional polarizing element, and an additional detector, wherein the additional optical element is configured to separate the scattered light in the other of the different segments into additional different segments of the collection numerical aperture, wherein the additional polarizing element is configured to separate the scattered light in one of the additional different segments into additional different portions of the scattered light based on polarization, and wherein the additional detector is configured to detect one of the additional different portions of the scattered light and to generate output responsive to the detected light.

30. The system of claim 29, wherein the different segments, the additional different segments, and any other different segments of the collection numerical aperture are complementary to each other such that in combination the detector, the additional detector, and any other detectors included in the system detect light across substantially the entire collection numerical aperture of the collection subsystem.

31. The system of claim 29, wherein the additional different portions of the light have orthogonal, mutually exclusive polarizations, and wherein the system further comprises another additional detector configured to detect another of the additional different portions of the scattered light.

32. The system of claim 1, further comprising a computer subsystem configured to use the output generated by the detector and output generated by at least one other detector included in the system to classify the defects detected on the wafer.

33. The system of claim 1, wherein configuring the optical element to separate the scattered light collected in the different segments of the collection numerical aperture optimizes the system for detection of at least one type of defect.

34. The system of claim 1, wherein configuring the polarizing element to separate the scattered light into the different portions is performed to maximize the signal-to-noise ratio detected by the detector for only a subset of the defects on the wafer.

35. The system of claim 1, further comprising relay optics configured to relay light from the Fourier plane of the collection subsystem to the conjugate of the Fourier plane and to control the size of the conjugate of the Fourier plane.

36. The system of claim 1, further comprising a computer subsystem configured to select one of multiple optical elements included in the system to be positioned at the Fourier plane or the conjugate of the Fourier plane of the collection subsystem and to control one or more elements of the system to move the selected optical element into position in the Fourier plane or the conjugate of the Fourier plane.

37. The system of claim 1, further comprising a field stop positioned in the path of the collected light, wherein the field stop is configured to reject light scattered from air molecules near a surface of the wafer in one or more paths of one or more light beams used by the illumination subsystem to illuminate the wafer.

38. The system of claim 1, wherein the system is further configured to scan light across the wafer by simultaneously rotating and translating the wafer.

39. A method for inspecting a wafer, comprising:
illuminating the wafer;
collecting light scattered from the wafer using a collection subsystem, wherein the collection subsystem is configured to preserve the polarization of the scattered light;
separating the scattered light collected in different segments of the collection numerical aperture of the collection subsystem using an optical element, wherein the optical element is positioned at a Fourier plane or a conjugate of the Fourier plane of the collection subsystem;

separating the scattered light in one of the different segments into different portions of the scattered light based on polarization using a polarizing element;

detecting one of the different portions of the scattered light to generate output responsive to the detected light; and detecting defects on the wafer using the output.

40. The method of claim 39, wherein the optical element and the polarizing element are configured to optimize detection of particles on the wafer by maximizing signal-to-noise ratio of scattering from particles detected in the detecting step and minimizing loss of signal corresponding to the particles detected in the detecting step due to the optical element and the polarizing element.

41. The method of claim 39, further comprising configuring the optical element to separate the scattered light collected in the different segments of the collection numerical aperture to optimize the method for detection of at least one type of defect and configuring the polarizing element to separate the scattered light into the different portions to maximize the signal-to-noise ratio detected by the detecting step for only a subset of the defects on the wafer.

42. The method of claim 39, further comprising using a field stop positioned in the path of the collected light to reject light scattered from air molecules near a surface of the wafer in one or more paths of one or more light beams used for said illuminating.

43. The method of claim 39, wherein the polarizing element has mirror symmetry with respect to an incident plane of said illuminating.

* * * * *